United States Patent
Alasia et al.

(10) Patent No.: US 8,178,687 B2
(45) Date of Patent: May 15, 2012

(54) DERIVATIVES OF PYRROLOINDOLE WHICH ARE INHIBITORS OF HSP90, COMPOSITIONS CONTAINING SAME, AND USE THEREOF

(75) Inventors: Marcel Alasia, Paris (FR); Hervé Minoux, Paris (FR); Jean-Marie Ruxer, Paris (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/970,458

(22) Filed: Dec. 16, 2010

(65) Prior Publication Data

US 2011/0184015 A1 Jul. 28, 2011

Related U.S. Application Data

(63) Continuation of application No. PCT/FR2009/051140, filed on Jun. 16, 2009.

(51) Int. Cl.
*C07D 215/38* (2006.01)

(52) U.S. Cl. .................. 548/181; 548/305.1; 548/312.1; 548/262.8; 548/428; 546/118; 546/121; 546/167; 546/276.7; 544/333

(58) Field of Classification Search ................. 548/428, 548/305.1, 312.1, 262.8, 181; 546/118, 121, 546/167, 276.7; 544/333
See application file for complete search history.

(56) References Cited

U.S. PATENT DOCUMENTS

2008/0119507 A1 5/2008 Mailliet et al.

FOREIGN PATENT DOCUMENTS

| EP | 1029854 | * | 1/2000 |
| FR | 2884252 A1 | | 10/2006 |
| WO | WO99/40094 | * | 8/1999 |
| WO | WO2006/123061 A2 | | 11/2006 |

OTHER PUBLICATIONS

Janin, Yves L., "Heat Shock Protein 90 Inhibitors. A Text Book Example of Medicinal Chemistry?" Journal of Medicinal Chemistry (2005), vol. 48, No. 24, pp. 7503-7511.
International Preliminary Report on Patentability dated Jan. 18, 2011 issued in PCT/FR2009/051140.

* cited by examiner

*Primary Examiner* — D M Seaman
(74) *Attorney, Agent, or Firm* — Scully, Scott, Murphy & Presser, P.C.

(57) ABSTRACT

Pyrroloindoles of formula (I) are provided wherein Het is an aromatic or partially unsaturated, monocyclic or bicyclic heterocycle containing between 1 and 4 heteroatoms N, O or S, optionally substituted by R1 or R'1 which are the same or different; R is X-(A-B)n-CONH2, X-(A-B)n-O—CONH2, X-(A-B)n-NH—CONH2, X—(CH2)m-heterocycloalkyl, X(CH2)m-aryl and X—(CH2)m-heteroaryl wherein X is —O—C(O), —NH—C(O), NH—CS, —NH—CO—CH2-O—; —NH—COCH2-S—CH2-CO—NH—; —NH—CO—(CH2)2-SO2-; and —NH—CO—CH2-N(CH3)-CO—; A and B are the same or different and are each independently a single bond, CH2, CH-alkyl, and CH-aralkyl; n=1, 2 and m=0, 1; R1 and/or R'1 are H, halogen, CF3, nitro, cyano, alkyle, hydroxy, mercapto, amino, alkylamino, dialkylamino, alkoxy, alkylthio, and carboxy, free or esterified by an alkyl, carboxamide, CONH(alkyl), CON(alkyl)2, NH—CO-alkyl, sulfonamide, NH—SO2-alkyl, S(O)2-NHalkyl, and S(O2)-N(alkyl)2 group, all of said alkyl, alcoxy and alkylthio groups being optionally substituted themselves, said products being in all isomer forms and salts, as medicaments.

8 Claims, No Drawings

DERIVATIVES OF PYRROLOINDOLE WHICH ARE INHIBITORS OF HSP90, COMPOSITIONS CONTAINING SAME, AND USE THEREOF

The present invention relates to novel chemical compounds which are heterocyclic derivatives of pyrrolo[1,2-a]indole, to the compositions which contain them, and to the use thereof as medicaments.

More particularly, according to a first aspect, the invention relates to novel heterocyclic derivatives of pyrrolo[1,2-a]indole displaying anticancer activity, and in particular Hsp90 chaperone protein-inhibiting activity, and more particularly via inhibition of the ATPase-type catalytic activity of the Hsp90 chaperone protein.

Chaperone Proteins:

The molecular chaperones of the "Heat Shock Protein" (HSP) family, which are classified according to their molecular weight (Hsp27, Hsp70, Hsp90, etc.) are key elements in the equilibrium between the synthesis and the degradation of cellular proteins responsible for correct protein folding. They play a vital role in response to cellular stress. HSPs, and in particular Hsp90, are also involved in the regulation of various very important functions of the cell, via their association with various client proteins involved in cell proliferation or apoptosis (Jolly C. and Morimoto R. I., J. N. Cancer Inst. (2000), 92, 1564-72; Smith D. F. et al., Pharmacological Rev. (1998), 50, 493-513; Smith D. F., Molecular Chaperones in the Cell, 165-178, Oxford University Press 2001).

Hsp90 Chaperone and Hsp90 Inhibitors in Cancer Treatment:

The Hsp90 chaperone, which represents 1 to 2% of the protein content of the cell, has recently been demonstrated as a particularly promising target in anticancer therapy (cf. for review: Moloney A. and Workman P., Expert Opin. Biol. Ther. (2002), 2(1), 3-24; Chiosis et al, Drug Discovery Today (2004), 9, 881-888). This interest relates in particular to the cytoplasmic interactions of Hsp90 with the main client proteins of Hsp90, which proteins are involved in the six mechanisms of tumour progression, as defined by Hanahan D. and Weinberg R. A. (Cell (2002), 100, 57-70), namely:

- an ability to proliferate in the absence of growth factors: EGFR-R/HER2, Src, Akt, Raf, MEK, Bcr-Abl, Flt-3, etc.,
- an ability to evade apoptosis: mutated form of p53, Akt, survivin, etc.,
- an insensitivity to signals to halt proliferation: Cdk4, Plk, Wee1, etc.,
- an ability to activate angiogenesis: VEGF-R, FAK, HIF-1, Akt, etc.,
- an ability to proliferate without replicative limit: hTert, etc.,
- an ability to invade new tissues and to metastasize: c-Met.

Among the other client proteins of Hsp90, steroid hormone receptors, such as the oestrogen receptor or the androgen receptor, are also of considerable interest in the context of anticancer therapies.

It has recently been shown that the alpha form of Hsp90 also has an extracellular role via its interaction with the MMP-2 metalloprotease, which is itself involved in tumour invasion (Eustace B. K. et al, Nature Cell Biology (2004), 6, 507-514).

Hsp90 is made up of two N- and C-terminal domains separated by a highly charged region. The dynamic interaction between these two domains, coordinated by the binding of nucleotides and of co-chaperones, determines the conformation of the chaperone and its state of activation. The association of the client proteins depends mainly on the nature of the co-chaperones Hsp70//Hsp40, Hop60, etc., and on the nature of the ADP or ATP nucleotide bound to the N-terminal domain of Hsp90. Thus, the hydrolysis of ATP to ADP and the ADP/ATP exchange factor control all of the chaperone "machinery", and it has been shown that it is sufficient to prevent the hydrolysis of ATP to ADP—ATPase activity of Hsp90—in order to release client proteins in the cytoplasm, which client proteins will then be degraded by the proteasome (Neckers L and Neckers K, Expert Opin. Emerging Drugs (2002), 7, 277-288; Neckers L, Current Medicinal Chemistry, (2003), 10, 733-739; Piper P. W., Current Opin. Invest. New Drugs (2001), 2, 1606-1610).

Role of Hsp90 and of Inhibitors Thereof in Pathologies Other than Cancer:

Various human pathologies are the consequence of incorrect folding of key proteins, resulting in particular in neurodegenerative diseases following the aggregation of certain proteins, such as in Alzheimer's disease and Huntington's disease or prion-related diseases (Tytell M. and Hooper P. L., Emerging Ther. Targets (2001), 5, 267-287). In these pathologies, approaches aimed at inhibiting Hsp90 for the purpose of activating the stress pathways (Hsp70, for example) could be beneficial (Nature Reviews Neuroscience 6: 11, 2005). Some examples are mentioned below:

i) Huntington's disease: This neurodegenerative disease is due to an extension of CAG triplets in exon 1 of the gene encoding the huntingtin protein. It has been shown that geldanamycin inhibits the aggregation of this protein due to the overexpression of the Hsp70 and Hsp40 chaperones (Human Molecular Genetics 10: 1307, 2001).

ii) Parkinson's disease: This disease is due to the progressive loss of dopaminergic neurons and is characterized by aggregation of the alpha-synuclein protein. It has been shown that geldanamycin is capable of protecting *drosophila* against the toxicity of alpha-synuclein on dopaminergic neurons.

iii) Focal cerebral ischaemia: It has been shown, in a rat animal model, that geldanamycin protects the brain against cerebral ischaemia, due to the effect of stimulation of the transcription of genes encoding the heat shock proteins by an Hsp90 inhibitor.

iv) Alzheimer's disease and multiple sclerosis: These diseases are due in part to the expression of pro-inflammatory cytokines and of the inducible form of NOS (Nitric Oxide Synthase) in the brain, and this harmful expression is suppressed by the response to stress. In particular, the Hsp90 inhibitors are capable of garnering this response to stress, and it has been shown, in vitro, that geldanamycin and 17-AAG exhibit anti-inflammatory activity in brain gliale cells (J. Neuroscience Res. 67: 461, 2002).

v) Amyotrophic lateral sclerosis: This neurodegenerative disease is due to the progressive loss of motor neurons. It has been shown that arimoclomol, an inducer of heat-shock proteins, delays the progression of the disease in an animal model (Nature Medicine 10: 402, 2004). Given that an Hsp90 inhibitor is also an inducer of heat-shock proteins (Mol. Cell. Biol. 19: 8033, 1999; Mol. Cell. Biol. 18: 4949, 1998), it is probable that a beneficial effect could also be obtained in this pathology for inhibitors of this type.

Furthermore, an inhibitor of the Hsp90 protein could potentially be of use in various diseases, other than cancer mentioned above, such as parasitic, viral or fungal diseases or neurodegenerative diseases, by virtue of a direct action on Hsp90 and specific client proteins. Some examples are given below:

vi) Malaria: the Hsp90 protein of *Plasmodium falciparum* exhibits 59% identity and 69% similarity with the human Hsp90 protein, and it has been shown that geldanamycin inhibits the growth of the parasite in vitro (Malaria Journal 2: 30, 2003; J. Biol. Chem. 278: 18336, 2003; J. Biol. Chem. 279: 46692, 2004).

vii) *Brugia* filariasis and Bancroft's filariasis: these lymphatic filarial parasites possess an Hsp90 protein which can potentially be inhibited with inhibitors of the human protein. In fact, it has been shown, for another similar parasite, *Brugia pahangi*, that the latter is sensitive to inhibition with geldanamycin. The *B. pahangi* and human sequences are 80% identical and 87% similar (Int. J. for Parasitology 35: 627, 2005).

viii) Toxoplasmosis: *Toxoplasma gondii*, the parasite responsible for toxoplasmosis, has an Hsp90 chaperone protein for which induction has been shown during tachyzoite-bradyzoite conversion, corresponding to passage from chronic infection to active toxoplasmosis. Furthermore, geldanamycin blocks this tachyzoite-bradyzoite conversion in vitro (J. Mol. Biol. 350: 723, 2005).

ix) Treatment-resistant mycoses: It is possible that the Hsp90 protein potentiates the evolution of drug resistance by allowing new mutations to develop. Consequently, an Hsp90 inhibitor, alone or in combination with another antifungal treatment, could prove to be of use in the treatment of certain resistant strains (Science 309: 2185, 2005). Furthermore, the anti-Hsp90 antibody developed by Neu Tec Pharma demonstrates an activity against *C. albicans*, which is sensitive and resistant to fluconazole, *C. krusei*, *C. tropicalis*, *C. glabrata*, *C. lusitaniae* and *C. parapsilosis* in vivo (Current Molecular Medicine 5: 403, 2005).

x) Hepatitis B: Hsp90 is one of the host proteins which interacts with the reverse transcriptase of the hepatitis B virus during the replication cycle of the virus. It has been shown that geldanamycin inhibits replication of the viral DNA and encapsulation of the viral RNA (Proc. Natl. Acad. Sci. USA 93: 1060, 1996).

xi) Hepatitis C: The human Hsp90 protein participates in the step consisting of cleavage between the NS2 and NS3 proteins by the viral protease. Geldanamycin and radicicol are capable of inhibiting this NS2/3 cleavage in vitro (Proc. Natl. Acad. Sci. USA 98: 13931, 2001).

xii) The Herpes virus: Geldanamycin has demonstrated inhibitory activities on HSV-1 virus replication in vitro, with a good therapeutic index (Antimicrobial Agents and Chemotherapy 48: 867, 2004). The authors have also found geldanamycin activity on the other viruses HSV-2, VSV, Cox B3, HIV-1 and the SARS coronavirus (data not shown).

xiii) Dengue (or tropical flu): It has been shown that the human Hsp90 protein participates in the virus entry step, by forming a complex also containing Hsp70 which serves as a receptor for the virus; an anti-Hsp90 antibody decreases the infectious capacity of the virus in vitro (J. of Virology 79: 4557, 2005)

xiv) Spinal and bulbar muscular atrophy (SBMA): A hereditary neurodegenerative disease characterized by an extension of CAG triplets in the androgen receptor gene. It has been shown that 17-AAG, a geldanamycin derivative, exhibits activity in vivo on transgenic animals used as experimental models for this disease (Nature Medicine 11: 1088, 2005).

Hsp90 Inhibitors:

The first known Hsp90 inhibitors are compounds of the amsamycin family, in particular geldanamycin (1) and herbimycin A. X-ray studies have shown that geldanamycin binds to the ATP site of the N-terminal domain of Hsp90, where it inhibits the ATPase activity of the chaperone (Prodromou C. et al, Cell (1997), 90, 65-75).

Currently, the NIH and Kosan BioSciences are carrying out the clinical development of 17-AAG (2), which is an Hsp90 inhibitor derived from geldanamycin (1), which blocks the ATPase activity of Hsp90 by binding to the N-terminal ATP recognition site. The results of phase I clinical trials for 17-AAG (1) have now led to phase II trials being started, but have also directed research towards derivatives which are more soluble, such as analogue 3 (17-DMAG from Kosan BioSciences), which carries a dimethyl amino chain in place of the methoxy residue, and towards optimized formulations of 17AAG (CNF1010 from Conforma Therapeutics):

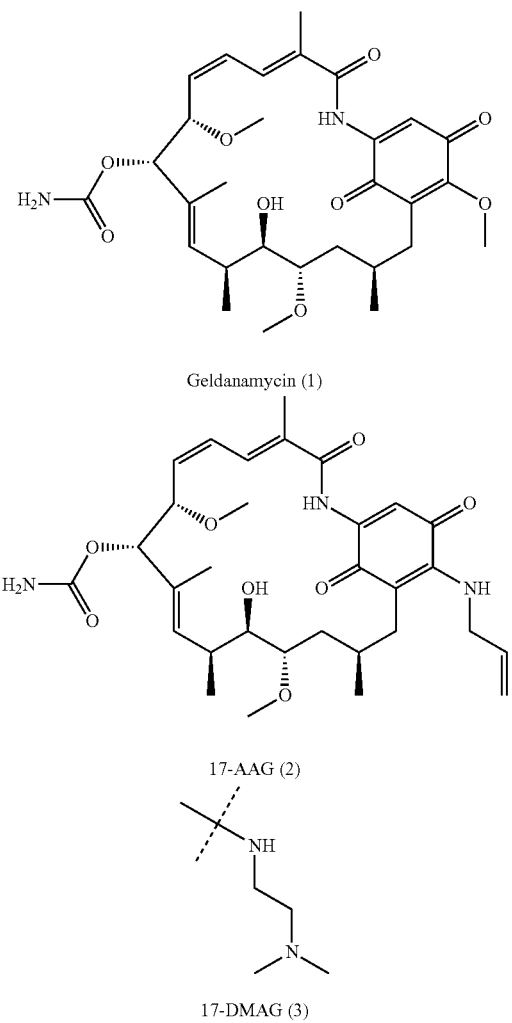

Geldanamycin (1)

17-AAG (2)

17-DMAG (3)

The reduced analogue of 17-AAG (WO 2005/063714/US 2006/019941) has also since relatively recently been undergoing phase I clinical studies by the company Infinity Pharmaceuticals. Novel geldanamycin derivatives or ansamycin derivatives have recently been described (WO2006/016773/ U.S. Pat. No. 6,855,705/US 2005/026894/WO2006/050477/

US2006/205705/WO2007/001049/WO2007/064926/
WO2007/074347/WO2007/098229/WO2007/128827/
WO2007/128829).

Radicicol (4) is also an Hsp90 inhibitor of natural origin (Roe S. M. et al, J. Med. Chem. (1999), 42, 260-66). However, although the latter is by far the best in vitro inhibitor of Hsp90, its metabolic instability with respect to sulphur-containing nucleophiles makes it difficult to use in vivo. Oxime derivatives that are much more stable, such as KF 55823 (5) or KF 25706, have been developed by the company Kyowa Hakko Kogyo (Soga et al, Cancer Research (1999), 59, 2931-2938).

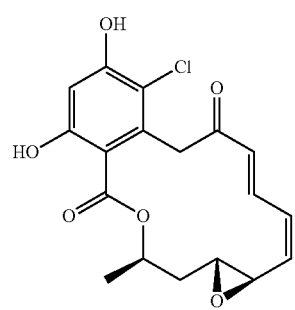

Radicicol (4)

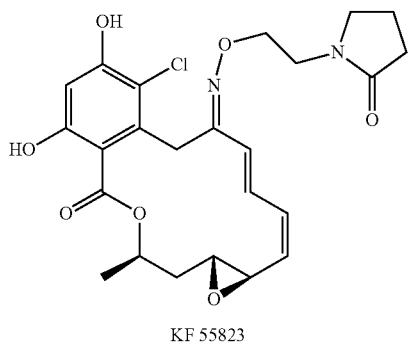

KF 55823 (5)

Structures of natural origin related to radicicol have also recently been described, such as zearalenone (6) by the company Conforma Therapeutics (WO 2003/041643) or compounds (7-9).

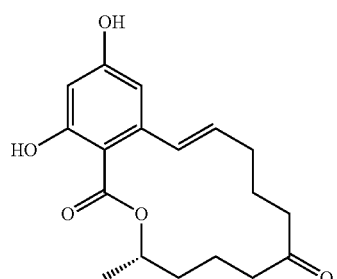

Zearalenone (6)

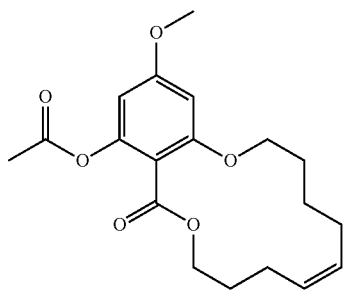

(7)

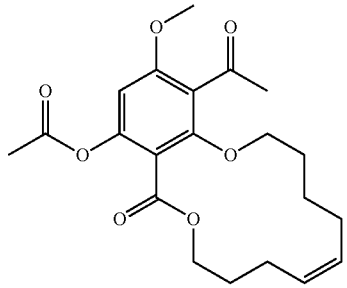

(8)

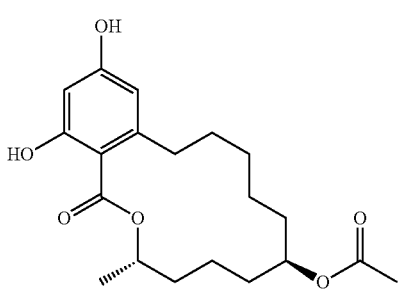

Zearalenone acetate (9)

Patent application US 2006/089495 describes mixed compounds comprising a quinone ring, such as the amsamycin derivatives, and a resorcinol ring, such as the radicicol analogues, as Hsp90 inhibitors.

An Hsp90 inhibitor of natural origin, novobiocin (10), binds to a different ATP site located in the C-terminal domain of the protein (Itoh H. et al, Biochem J. (1999), 343, 697-703). Simplified analogues of novobiocin have recently been identified as more powerful inhibitors of Hsp90 than novobiocin itself (J. Amer. Chem. Soc. (2005), 127(37), 12778-12779).

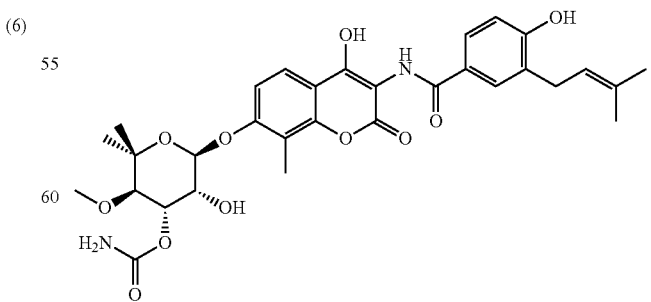

(10)

Patent applications WO2006/050501 and US2007/270452 claim novobiocin analogues as Hsp90 inhibitors.

Patent application WO2007/117466 claims derivatives of celastrol and of gedunine as Hsp90 inhibitors.

A depsipeptide, called pipalamycin or ICI101, has also been described as a non-competitive inhibitor of the ATP site of Hsp90 (J. Pharmacol. Exp. Ther. (2004), 310, 1288-1295).

Sherperdine, a KHSSGCAFL nonapeptide, mimics a part of the K79-K90 sequence (KHSSGCAFLSVK) of survivin and blocks the interaction of proteins of the IAP family with Hsp90 in vitro (WO 2006/014744).

Small peptides, comprising a sequence of otoferlin-type (YSLPGYMVKKLLGA), have recently been described as Hsp90 inhibitors (WO 2005/072766).

Purines, such as the compounds PU3 (11) (Chiosis et al, Chem. Biol. (2001), 8, 289-299) and PU24FCI (12) (Chiosis et al, Curr. Canc. Drug

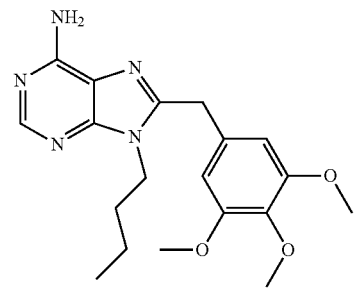

(11)

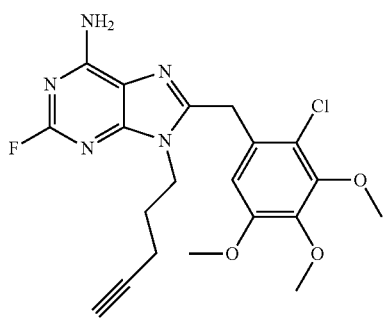

(12)

Targets (2003), 3, 371-376; WO 2002/036075) have also been described as Hsp90 inhibitors:

A purine derivative, CNF2024 (13), has recently been introduced clinically by the company Conforma therapeutics, in collaboration with the Sloan Kettering Memorial Institute for Cancer Research (WO 2006/084030).

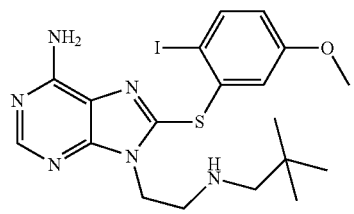

(13)

Patent application FR 2880540 (Aventis) claims another family of Hsp90-inhibiting purines.

Patent application WO 2004/072080 (Cellular Genomics) claims a family of 8-heteroaryl-6-phenylimidazo[1,2-a]pyrazines as modulators of hsp90 activity.

Patent application WO 2004/028434 (Conforma Therapeutics) claims aminopurines, aminopyrrolopyrimidines, aminopyrazolopyrimidines and aminotriazolopyrimidines as Hsp90 inhibitors.

Patent application WO 2004/050087 (Ribotarget/Vernalis) claims a family of pyrazoles that can be used for treating pathologies related to the inhibition of heat-shock proteins such as the Hsp90 chaperone.

Patent application WO 2004/056782 (Vernalis) claims a novel family of pyrazoles that can be used for treating pathologies related to the inhibition of heat-shock proteins such as the Hsp90 chaperone.

Patent application WO 2004/07051 (Vernalis) claims aryl-isoxazole derivatives that can be used for treating pathologies related to the inhibition of heat-shock proteins such as the Hsp90 chaperone.

Patent application WO 2004/096212 (Vernalis) claims a third family of pyrazoles that can be used for treating pathologies related to the inhibition of heat-shock proteins such as the Hsp90 chaperone.

Patent application WO 2005/00300 (Vernalis) claims, more generally, 5-membered heterocycles, substituted with aryl radicals, that can be used for treating pathologies related to the inhibition of heat-shock proteins such as the Hsp90 chaperone.

Patent application JP 2005/225787 (Nippon Kayaku) claims another family of pyrazoles as Hsp90 inhibitors.

Patent application WO2005/00778 (Kyowa Hakko Kogyo) claims a family of benzophenone derivatives as Hsp90 inhibitors, that can be used for the treatment of tumours.

Patent application WO2005/06322 (Kyowa Hakko Kogyo) claims a family of resorcinol derivatives as Hsp90 inhibitors.

Patent application WO2005/051808 (Kyowa Hakko Kogyo) claims a family of resorcinylbenzoic acid derivatives as Hsp90 inhibitors.

Patent applications WO2005/021552, WO2005/0034950, WO2006/08503, WO2006/079789 and WO2006/090094 (Vernalis) claim families of pyrimidothiophenes or of pyridothiophenes, that can be used for treating pathologies related to the inhibition of heat-shock proteins such as the Hsp90 chaperone.

Application WO2006/018082 (Merck) claims another family of pyrazoles as Hsp90 inhibitors.

Application WO2006/010595 (Novartis) claims a family of indazoles as Hsp90 inhibitors.

Application WO2006/010594 (Novartis) claims a family of dihydrobenzimidazolones as Hsp90 inhibitors.

Patent application WO2006/055760 (Synta Pharma) claims a family of diaryltriazoles as Hsp90 inhibitors.

Patent application WO2006/087077 (Merck) claims a family of (s-triazol-3-yl)phenols as Hsp90 inhibitors.

Patent application FR2882361 (Aventis) claims a family of 3-aryl-1,2-benzisoxazoles as Hsp90 inhibitors.

Patent application WO2006/091963 (Serenex) claims families of tetrahydroindolones and of tetrahydroindazolones as Hsp90 inhibitors.

Patent application DE10200509440 (Merck) claims a family of thienopyridines as Hsp90 inhibitors.

Patent application WO2006/095783 (Nippon Kayaku) claims a family of triazoles as Hsp90 inhibitors.

Patent application WO2006/101052 (Nippon Kayaku) claims a family of acetylene derivatives as Hsp90 inhibitors.

Patent application WO2006/105372 (Conforma Therapeutics) claims a family of alkynyl pyrrolo[2,3-d]pyrimidines as Hsp90 inhibitors.

Patent application FR2884252 (Aventis) claims a family of isoindoles as Hsp90 inhibitors.

Patent application WO2006/1009075 (Astex Therapeutics) claims a family of benzamides as Hsp90 inhibitors.

Patent application WO2006/109085 (Astex Therapeutics) claims a family of hydroxybenzamides as Hsp90 inhibitors.

Patent application WO2006/113498 (Chiron) claims a family of 2-aminoquinazolin-5-ones as Hsp90 inhibitors.

Patent application JP200606755 (Nippon Kayaku) claims a family of pyrazoles as Hsp90 inhibitors.

Patent application WO2006/117669 (Pfizer) claims a family of hydroxyarylcarboxamides as Hsp90 inhibitors.

Patent applications WO2006/122631 and DE102006008890 (Merck GmbH) claim a family of amino-2-phenyl-4-quinazolines as Hsp90 inhibitors.

Patent application WO2006/123061 (Aventis) claims a family of azabenzimidazolylfluorene or benzimidazolylfluorene derivatives as Hsp90 inhibitors.

Patent application WO2006/123065 (Astex Therapeutics) claims a family of azinamines (amino-2-pyrimidines or triazines) as Hsp90 inhibitors.

Patent application WO2006/125531 (Merck GmbH) claims a family of thieno[2,3b]pyridines as Hsp90 inhibitors.

Patent applications WO2006/125813 and WO2006/125815 (Altana Pharma) claim a family of tetrahydropyridothiophenes as Hsp90 inhibitors.

Patent application WO2007/017069 (Merck GmbH) claims a family of adenine derivatives as Hsp90 inhibitors.

Patent applications WO2007/021877 and WO2007/01966 (Synta Pharma) claim, respectively, families of arylpyrazoles and of arylimidazoles as Hsp90 inhibitors.

Patent application WO2007/022042 (Novartis) claims a family of pyrimidylaminobenzamides as Hsp90 inhibitors.

Patent application WO2007/034185 (Vernalis) claims a family of heteroarylpurines as Hsp90 inhibitors.

Patent application WO2007/041362 (Novartis) claims a family of 2-amino-7,8-dihydro-6H-pyrido[4,3-d]pyrimidin-5-ones as Hsp90 inhibitors.

Patent application WO2007/104944 (Vernalis) claims a family of pyrrolo[2,3b]pyridines as Hsp90 inhibitors.

Patent application US2007/105862 claims a family of azole derivatives as Hsp90 inhibitors.

Patent application WO2007/129062 (Astex Therapeutics) claims a family of diazoles (aryl pyrazoles) as Hsp90 inhibitors.

Patent application US2007/129334 (Conforma Therapeutics) claims a family of arylthiopurines as Hsp90 inhibitors, which are active orally.

Patent application WO2007/155809 (Synta Pharma) claims families of phenyltriazoles as Hsp90 inhibitors.

Patent application WO2007/092496 (Conforma Therapeutics) claims a family of 7,9-dihydropurin-8-ones as Hsp90 inhibitors.

Patent application WO2007/207984 (Serenex) claims a family of cyclohexylaminobenzene derivatives as Hsp90 inhibitors.

Patent applications DE10206023336 and DE10206023337 (Merck GmbH) claim, respectively, families of 1,5-diphenylpyrazoles and of 1,5-diphenyltriazoles as Hsp90 inhibitors.

Patent application WO2007/134298 (Myriad Genetics) claims a family of purinamines as Hsp90 inhibitors.

Patent application WO2007/138994 (Chugai) claims families of 2-aminopyrimidines or of 2-aminotriazines as Hsp90 inhibitors.

Patent applications WO2007/139951, WO2007/139952, WO2007/139960, WO2007/139967, WO2007/139968, WO2007/139955 and WO2007/140002 (Synta Pharma) claim families of triazoles as Hsp90 inhibitors and agents for treating non-Hodgkin's lymphomas.

The present invention relates to pyrrolo[1,2-a]indole derivatives which are products of formula (I)

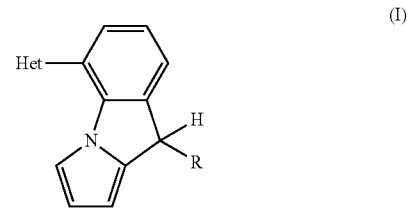

in which:

Het represents a monocyclic or bicyclic, aromatic or partially unsaturated heterocycle—of dihydro or tetrahydro type—, with from 5 to 11 ring members, containing from 1 to 4 heteroatoms chosen from N, O or S, optionally substituted with one or more radicals R1 or R'1, which may be identical or different, as described below, R is chosen from the group constituted of X-(A-B)$_n$—CONH$_2$, X-(A-B)$_n$—O—CONH$_2$, X-(A-B)$_n$—NH—CONH$_2$, X—(CH$_2$)$_m$-heterocycloalkyl, X—(CH$_2$)$_m$-aryl and X—(CH$_2$)$_m$-heteroaryl where X represents —O—C(O), —NH—C(O), NH—CS, —NH—CO—CH$_2$—O—; —NH—CO—CH$_2$—S—CH$_2$—CO—NH—; —NH—CO—(CH$_2$)$_2$—SO$_2$—; —NH—CO—CH$_2$—N(CH$_3$)—CO—; A and B, which may be identical or different, independently represent a single bond, CH$_2$, CH-alkyl or CH-aralkyl, n=1 or 2 and m=0 or 1;

R1 and/or R'1, which may be identical or different, are in the group constituted of H, halogen, CF$_3$, nitro, cyano, alkyl, hydroxyl, mercapto, amino, alkylamino, dialkylamino, alkoxy, phenylalkoxy, alkylthio, carboxyl in free form or esterified with an alkyl radical, carboxamide, CO—NH(alkyl), CON(alkyl)$_2$, NH—CO-alkyl, sulphonamide, NH—SO$_2$-alkyl, S(O)$_2$—NHalkyl and S(O$_2$)—N(alkyl)$_2$, all the alkyl, alkoxy and alkylthio radicals being themselves optionally substituted with one or more radicals, which may be identical or different, chosen from halogen, hydroxyl, alkoxy, amino, alkylamino and dialkylamino;

said products of formula (I) being in all the possible tautomeric and isomeric forms: racemic, enantiomeric and diastereoisomeric, and also as addition salts with inorganic and organic acids or with inorganic and organic bases of the products of formula (I), and also the prodrugs of the products of general formula (I).

In the products of formula (I) and in the subsequent text, the terms indicated have the meanings which follow:

The term "halogen" denotes fluorine, chlorine, bromine or iodine atoms, and preferably fluorine, chlorine or bromine.

The term "alkyl radical" denotes a linear or branched radical containing at most 12 carbon atoms, chosen from methyl, ethyl, propyl, isopropyl, butyl, isobutyl, sec-butyl, tert-butyl, pentyl, isopentyl, sec-pentyl, tert-pentyl, neopentyl, hexyl, isohexyl, sec-hexyl, tert-hexyl and also heptyl, octyl, nonyl, decyl, undecyl and dodecyl radicals, and also the linear or branched positional isomers thereof. Mention may more particularly be made of alkyl radicals having at most 6 carbon atoms, and in particular the following radicals: methyl, ethyl, propyl, isopropyl, n-butyl, isobutyl, tert-butyl, pentyl, which may be linear or branched, and hexyl, which may be linear or branched.

The term "alkoxy radical" denotes a linear or branched radical containing at most 12 carbon atoms, and preferably 6 carbon atoms, chosen, for example, from the following radicals: methoxy, ethoxy, propoxy, isopropoxy, linear, secondary or tertiary butoxy, pentoxy, hexoxy or heptoxy, and also the linear or branched positional isomers thereof.

The term "alkylthio" or "alkyl-S-" denotes a linear or branched radical containing at most 12 carbon atoms and represents in particular methylthio, ethylthio, isopropylthio and heptylthio radicals. In the radicals containing a sulphur atom, the sulphur atom may be oxidized to an SO or $S(O)_2$ radical.

The term "carboxamide" denotes $CONH_2$.

The term "sulphonamide" denotes $SO_2NH_2$.

The term "acyl or r-CO— radical" denotes a linear or branched radical containing at most 12 carbon atoms, in which the radical r represents a hydrogen atom or an alkyl, cycloalkyl, cycloalkenyl, heterocycloalkyl or aryl radical, these radicals having the values indicated above and being optionally substituted as indicated: mention is made, for example, of formyl, acetyl, propionyl, butyryl or benzoyl radicals, or else valeryl, hexanoyl, acryloyl, crotonoyl or carbamoyl radicals.

The term "cycloalkyl radical" denotes a monocyclic or bicyclic, carbocyclic radical containing from 3 to 10 ring members and denotes in particular cyclopropyl, cyclobutyl, cyclopentyl and cyclohexyl radicals.

The term "cycloalkylalkyl radical" denotes a radical in which cycloalkyl and alkyl are chosen from the values indicated above: this radical thus denotes, for example, cyclopropylmethyl, cyclopentylmethyl, cyclohexylmethyl and cycloheptylmethyl radicals.

The term "acyloxy radical" is intended to mean acyl-O— radicals in which acyl has the meaning indicated above: mention is made, for example, of acetoxy or propionyloxy radicals.

The term "acylamino radical" is intended to mean acyl-N— radicals in which acyl has the meaning indicated above.

The term "aryl radical" denotes carbocyclic unsaturated radicals which are monocyclic or consist of condensed rings. As examples of such an aryl radical, mention may be made of phenyl or naphthyl radicals.

The term "arylalkyl" is intended to mean radicals resulting from the combination of the alkyl radicals mentioned above, which are optionally substituted, and the aryl radicals also mentioned above, which are optionally substituted: mention is, for example, made of benzyl, phenylethyl, 2-phenethyl, triphenylmethyl or naphthlenemethyl radicals.

The term "heterocyclic radical" denotes a saturated (heterocycloalkyl) or partially or completely unsaturated (heteroaryl) carbocyclic radical consisting of 4 to 10 ring members interrupted with one or more heteroatoms, which may be identical or different, chosen from oxygen, nitrogen or sulphur atoms.

As heterocycloalkyl radicals, mention may in particular be made of dioxolane, dioxane, dithiolane, thiooxolane, thiooxane, oxirannyl, oxolannyl, dioxolannyl, piperazinyl, piperidyl, pyrrolidinyl, imidazolidinyl, imidazolidine-2,4-dione, pyrazolidinyl, morpholinyl, tetrahydrofuryl, hexahydropyran, tetrahydrothienyl, chromanyl, dihydrobenzofuranyl, indolinyl, perhydropyranyl, pyrindolinyl, tetrahydroquinolinyl, tetrahydroisoquinolinyl or thioazolidinyl radicals, all these radicals being optionally substituted.

Among the heterocycloalkyl radicals, mention may in particular be made of optionally substituted piperazinyl, N-methylpiperazinyl, optionally substituted piperidyl, optionally substituted pyrrolidinyl, imidazolidinyl, pyrazolidinyl, morpholinyl, hexahydropyran or thiazolidinyl radicals.

The term "heterocycloalkylalkyl radical" is intended to mean radicals in which the heterocycloalkyl and alkyl residues have the meanings above.

Among the heteroaryl radicals with 5 ring members, mention may be made of furyl, pyrrolyl, tetrazolyl, thiazolyl, isothiazolyl, diazolyl, thiadiazolyl, thiatriazolyl, oxazolyl, oxadiazolyl, isoxazolyl, imidazolyl, pyrazolyl, thienyl and triazolyl radicals.

Among the heteroaryl radicals with 6 ring members, mention may in particular be made of pyridyl radicals such as 2-pyridyl, 3-pyridyl and 4-pyridyl, pyrimidyl radicals, pyridazinyl radicals and pyrazinyl radicals.

As condensed heteroaryl radicals containing at least one heteroatom chosen from sulphur, nitrogen and oxygen, mention may, for example, be made of benzothienyl, benzofuryl, benzopyrrolyl, benzothiazolyl, benzimidazolyl, imidazopyridyl, imidazopyrimidinyl, imidazopyrazinyl, purinyl, pyrrolopyrimidinyl, pyrolopyridinyl, benzoxazolyl, benzisoxazolyl, benzisothiazolyl, thionaphtyl, chromenyl, indolizinyl, quinazolinyl, quinoxalinyl, indolyl, indazolyl, purinyl, quinolyl, isoquinolyl and naphthyridinyl.

The term "alkylamino radical" is intended to mean radicals in which the alkyl radical is chosen from the alkyl radicals mentioned above. Preference is given to alkyl radicals having at most 4 carbon atoms, and mention may, for example, be made of methylamino, ethylamino, propylamino or linear or branched butylamino radicals.

The term "dialkylamino radical" is intended to mean radicals in which the alkyl radicals, which may be identical or different, are chosen from the alkyl radicals mentioned above. As above, preference is given to alkyl radicals having at most 4 carbon atoms, and mention may, for example, be made of dimethylamino radicals, diethylamino radicals or methylethylamino radicals, which may be linear or branched.

The term "patient" denotes human beings, but also other mammals.

The term "prodrug" denotes a product which can be converted in vivo, by metabolic mechanisms (such as hydrolysis), to a product of formula (I). For example, an ester of a product of formula (I) containing a hydroxyl group can be converted by hydrolysis, in vivo, to its parent molecule. Alternatively, an ester of a product of formula (I) containing a carboxyl group can be converted by hydrolysis, in vivo, to its parent molecule.

By way of examples, mention may be made of esters of products of formula (I) containing a hydroxyl group, such as acetates, citrates, lactates, tartrates, malonates, oxalates, salicylates, propionates, succinates, fumarates, maleates, methylene-bis-beta-hydroxynaphthoates, gentisates, isethionates, di-p-toluoyl tartrates, methanesulphonates, ethanesulphonates, benzenesulphonates, p-toluenesulphonates, camphorsulphonates, cyclohexylsulphamates and quinates.

Particularly useful esters of products of formula (I) containing a hydroxyl group can be prepared from acid residues such as those described by Bundgaard et. al., J. Med. Chem., 1989, 32, page 2503-2507: these esters include, in particular, substituted (aminomethyl)benzoates, dialkylamino-methyl benzoates in which the two alkyl groups can be linked together or can be interrupted with an oxygen atom or with an optionally substituted nitrogen atom, i.e. an alkylated nitrogen atom, or else (morpholinomethyl)benzoates, e.g. 3- or 4-(morpholinomethyl)benzoates, and (4-alkylpiperazin-1-yl)benzoates, e.g. 3- or 4-(4-alkylpiperazin-1-yl)benzoates.

The carboxyl radical(s) of the products of formula (I) can be salified or esterified.

It may be recalled that stereoisomerism can be defined, in its broad sense, as the isomerism of compounds having the same structural formulae, but the various groups of which are arranged differently in space, such as, in particular, in monosubstituted cyclohexanes in which the substituent can be in the axial or equatorial position, and the various possible rotational conformations of ethane derivatives. However, another type of stereoisomerism exists, due to the different spatial arrangements of attached substituents, either on double bonds or on rings, which is often referred to as geometric isomerism or cis-trans isomerism. The term "stereoisomer" is used, in the present application, in its broadest sense and therefore relates to all the compounds indicated above.

The present invention thus relates in particular to the products of formula (I) as defined above, in which Het represents a heterocycle as defined above containing in particular at least one nitrogen atom and optionally substituted with one or more radicals R1 or R'1, which may be identical or different, as defined above, and R having any one of the definitions indicated above or hereinafter, said products of formula (I) being in all the possible tautomeric and isomeric forms: racemic, enantiomeric and diastereoisomeric, and also as addition salts with inorganic and organic acids or with inorganic and organic bases of the products of formula (I), and also the prodrugs of the products of general formula (I).

The present invention thus relates in particular to the products of formula (I) as defined above in which:
Het is chosen from the group constituted of:

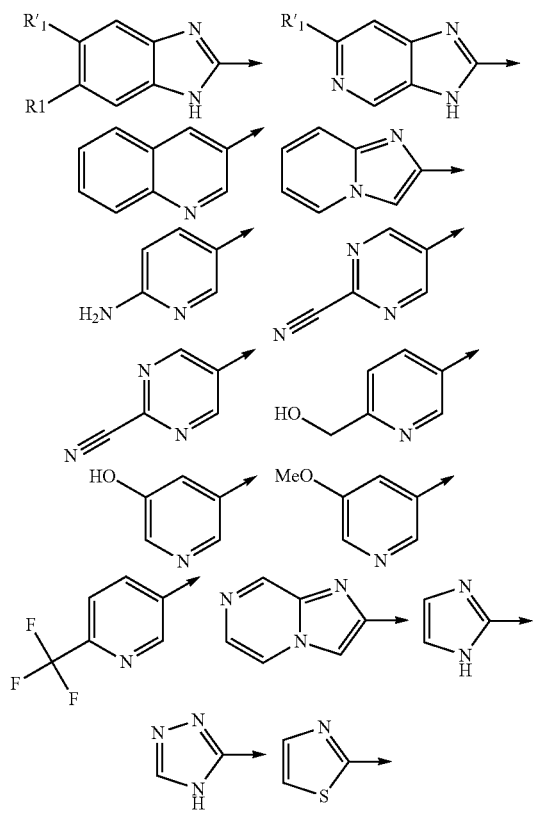

R1 and/or R'1, which may be identical or different, are in the group constituted of H, halogen, $CF_3$, nitro, cyano, alkyl, hydroxyl, mercapto, amino, alkylamino, dialkylamino, alkoxy, alkylthio (methylthio), carboxyl in free form or esterified with an alkyl radical, carboxamide, CO—NH(alkyl), CON(alkyl)$_2$, NH—CO-alkyl, sulphonamide, NH—$SO_2$-alkyl, $S(O)_2$—NH(alkyl) and $S(O)_2$—N(alkyl)$_2$, all the alkyl, alkoxy and alkylthio radicals being themselves optionally substituted with one or more radicals, which may be identical or different, chosen from halogen, hydroxyl, alkoxy, amino, alkylamino and dialkylamino;

the substituent R of said products of formula (I) being chosen from the values defined above or hereinafter, said products of formula (I) being in all the possible tautomeric and isomeric forms: racemic, enantiomeric and diastereoisomeric, and also as addition salts with inorganic and organic acids or with inorganic and organic bases of the products of formula (I), and also the prodrugs of the products of general formula (I).

The present invention thus relates in particular to the products of formula (I) as defined above, in which Het represents a heterocycle as defined above, optionally substituted with one or more radicals R1 or R'1, which may be identical or different, as defined above, and R represents in particular the X—(CH$_2$)$_m$-heteroaryl group as defined above or hereinafter, where X represents in particular —NH—CO— and m represents in particular 0, said products of formula (I) being in all the possible tautomeric and isomeric forms: racemic, enantiomeric and diastereoisomeric, and also as addition salts with inorganic and organic acids or with inorganic and organic bases, of the products of formula (I), and also the prodrugs of the products of general formula (I).

The present invention thus relates in particular to the products of formula (I) as defined above, in which Het represents a heterocycle as defined above, optionally substituted with one or more radicals R1 or R'1, which may be identical or different, as defined above, and R is chosen from the group constituted of:

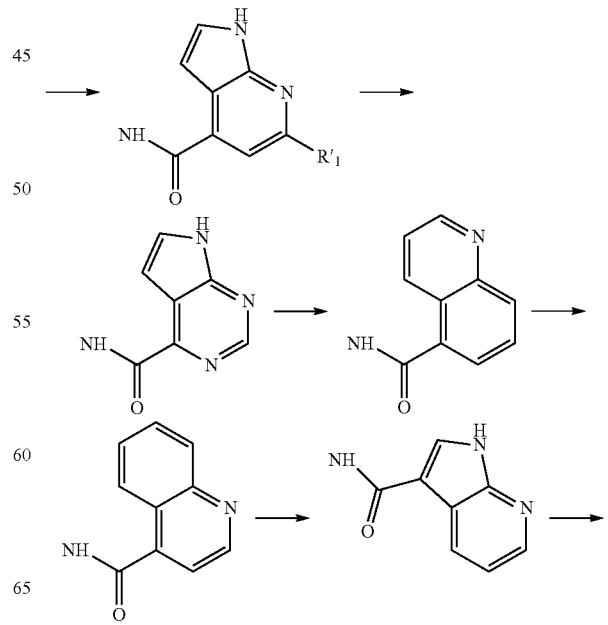

-continued

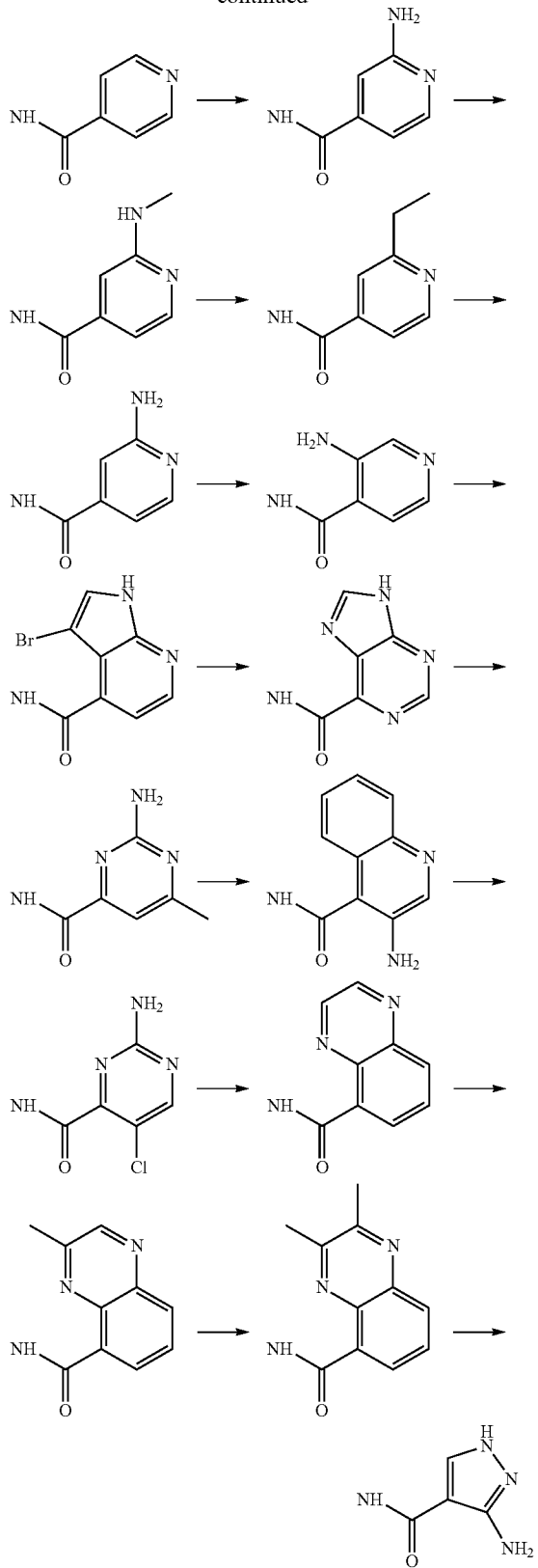

said products of formula (I) being in all the possible tautomeric and isomeric forms: racemic, enantiomeric and diastereoisomeric, and also as addition salts with inorganic and organic acids or with inorganic and organic bases of the products of formula (I), and also the prodrugs of the products of general formula (I).

The present invention thus relates in particular to the products of formula (I) as defined above or hereinafter, in which:

Het is chosen in the group constituted of:

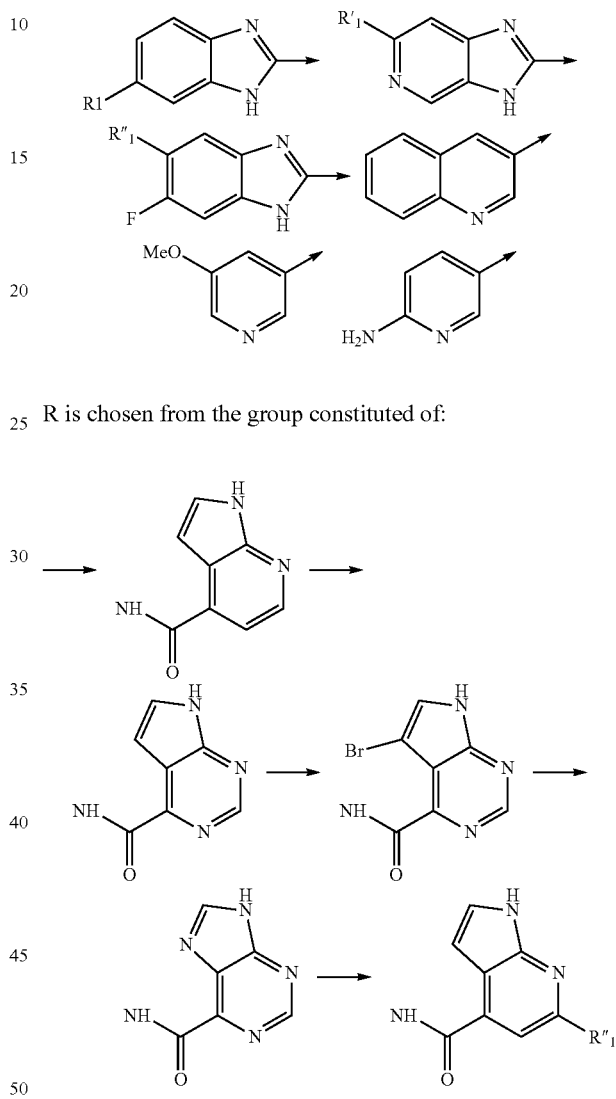

R is chosen from the group constituted of:

R1 is chosen from the group constituted of H, F, Cl, Br, $CF_3$, $NO_2$, CN, $CH_3$, OH, $OCH_3$, $OCF_3$, $CO_2Me$, $CONH_2$, CONHMe, CONH—$(CH_2)_3$—OMe, CONH—$(CH_2)_3$—$N(Me)_2$, NHC(O)Me, $SO_2NH_2$ and $SO_2N(Me)_2$;

R'1 is in the group constituted of H, $CONH_2$, CONHMe and OMe;

R"1 is in the group constituted of F, Cl, OH, OMe, CN, O—$(CH_2)_3$—OMe and O—$(CH_2)_3$—$N(Me)_2$;

said products of formula (I) being in all the possible tautomeric and isomeric forms: racemic, enantiomeric and diastereoisomeric, and also as addition salts with inorganic and organic acids or with inorganic and organic bases of the products of formula (I), and also the prodrugs of the products of general formula (I).

The present invention thus relates in particular to the products of formula (I) as defined above or hereinafter, in which:
Het is chosen from the group constituted of:

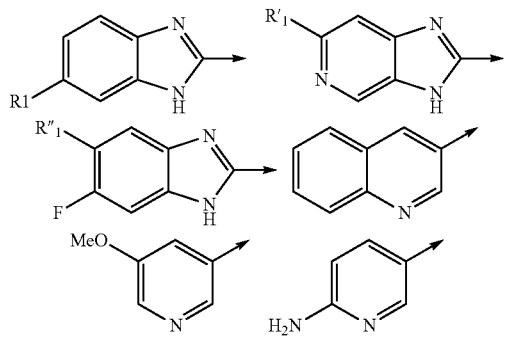

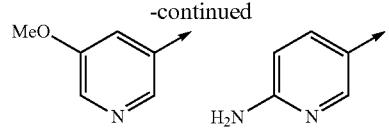

with:
R1 represents H, F, Cl, Br, CF$_3$, NO$_2$, CN, CH$_3$, OH, OCH$_3$, OCF$_3$, CO$_2$Me, CONH$_2$, CONHMe, CONH—(CH$_2$)$_3$—OMe, CONH—(CH$_2$)$_3$—N(Me)$_2$, NHC(O)Me, SO$_2$NH$_2$ or SO$_2$N(Me)$_2$;
R'1 represents H, CONH$_2$, CONHMe or OMe;
R"1 represents F, Cl, OH, OMe, CN, O—(CH$_2$)$_3$—OMe or O—(CH$_2$)$_3$—N(Me)$_2$;
and R is chosen from the group constituted of:

R is chosen from the group constituted of:

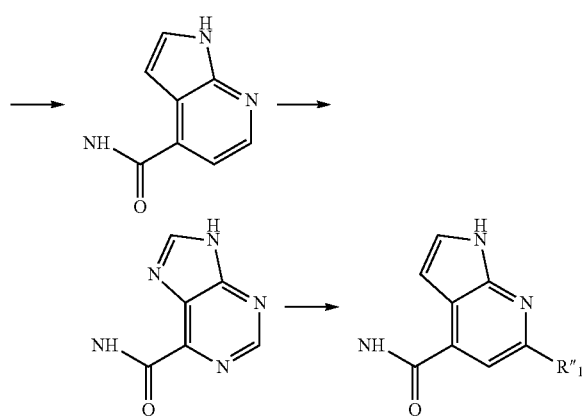

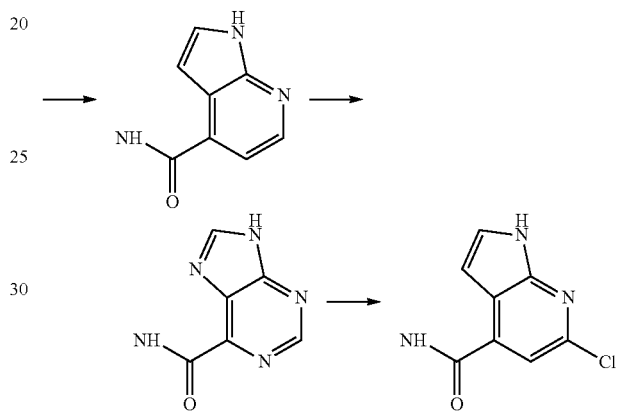

R1 is in the group constituted of H, F, Cl, Br, CF$_3$, NO$_2$, CN, CH$_3$, OH, OCH$_3$, OCF$_3$, CO$_2$Me, CONH$_2$, CONHMe, CONH—(CH$_2$)$_3$—OMe, CONH—(CH$_2$)$_3$—N(Me)$_2$, NHC(O)Me, SO$_2$NH$_2$ and SO$_2$N(Me)$_2$;
R'1 is in the group constituted of H, CONH$_2$, CONHMe and OMe;
R"1 is in the group constituted of F, Cl, OH, OMe, CN, O—(CH$_2$)$_3$—OMe and O—(CH$_2$)$_3$—N(Me)$_2$;
said products of formula (I) being in all the possible isomeric forms: racemic, enantiomeric and diastereoisomeric; and also the addition salts with inorganic and organic acids or with inorganic and organic bases.

A subject of the invention is in particular the products of formula (I) as defined above, in which:
Het is chosen from the group constituted of:

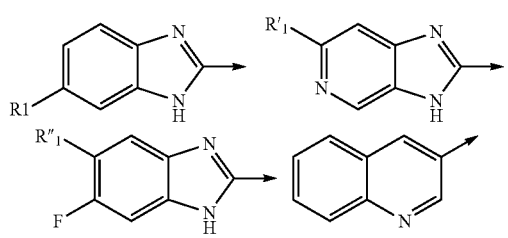

and also the prodrugs thereof, said products of formula (I) being in all the possible isomeric forms: tautomeric, racemic, enantiomeric and diastereo-isomeric, and also the addition salts with inorganic and organic acids or with inorganic and organic bases of said products of formula (I).

A subject of the present invention is more particularly the products of formula (I) as defined above, the names of which are given below:
1H-pyrrolo[2,3-b]pyridine-4-carboxylic acid [5-(6-fluoro-1H-benzimidazol-2-yl)-9H-pyrrolo[1,2-a]indol-9-yl] amide,
1H-pyrrolo[2,3-b]pyridine-4-carboxylic acid (5-quinolin-3-yl-9H-pyrrolo[1,2-a]indol-9-yl)amide,
1H-pyrrolo[2,3-b]pyridine-4-carboxylic acid [5-(3H-imidazo[4,5-c]pyridin-2-yl)-9H-pyrrolo[1,2-a]indol-9-yl] amide,
6-chloro-1H-pyrrolo[2,3-b]pyridine-4-carboxylic acid [5-(3H-imidazo[4,5-c]pyridin-2-yl)-9H-pyrrolo[1,2-a]indol-9-yl]amide,
and also the addition salts with inorganic and organic acids or with inorganic and organic bases of said products of formula (I).

The products of formula (I) according to the present invention can be prepared according to the methods known to those skilled in the art and particularly according to the methods described hereinafter: a subject of the present invention is thus also the methods for synthesizing the products of formula (I) according to the present invention, and in particular the general methods of synthesis described in the schemes hereinafter.

General Methods of Synthesis of Compounds of General Formula (I):

The products of general formula (I) can be prepared from a derivative of general formula (II), either by using a derivative of general formula (III) (method A) or by using a derivative of general formula (IV) (method B) according to general scheme (1) below:

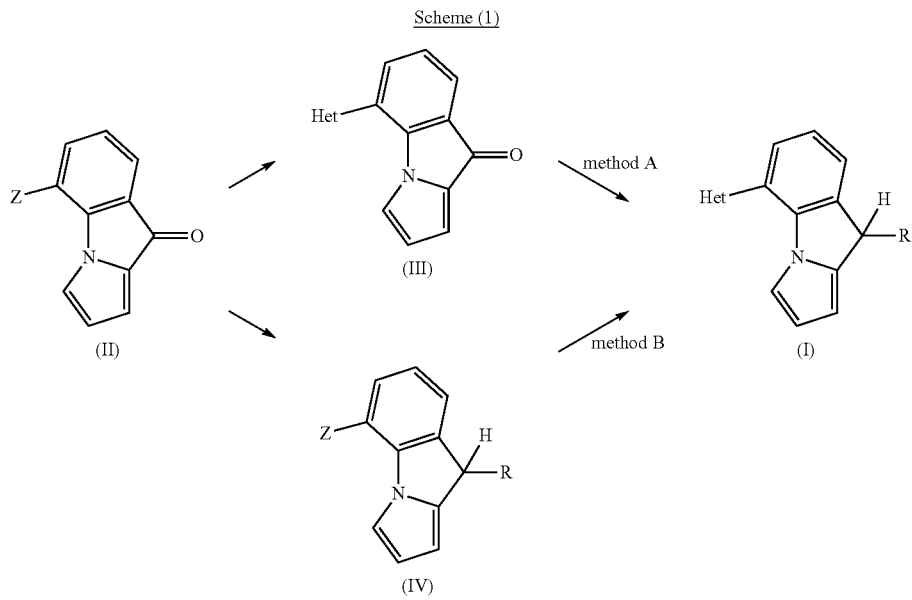

Scheme (1)

Z = OTf, I, Br, B(OH)₂ or B(OR)₂* or C(O)—OMe, C(O)—OH or C(O)—H) or OH or O—CH₂—Ph
*B(OR)₂ being able to form a ring A subject of the present invention is thus in particular a process for preparing the products of formula (I) as defined above, characterized by scheme (I) above, according to which the products of general formula (I) can be prepared from a derivative of general formula (II), either by using a derivative of general formula (III) (method A) or by using a derivative of general formula (IV) (method B) and in which the substituents Het and R have the meanings indicated above for the products of formula (I) and z has the meaning indicated above in Scheme (1).

A subject of the present invention is also the methods for preparing the products of formula (I), and intermediates for obtaining products of formula (I), according to schemes 2 to 12 hereinafter.

Preparation of the Compounds of General Formula (II)

A subject of the present invention is thus also the methods for synthesizing the products of formula (II), in which Z represents bromine, the triflate radical, a boronic acid or a boronate, which is optionally cyclic, a carboxyl radical, a methyl carboxylate radical, a hydroxyl radical or a benzyloxy radical.

The product of general formula (II) in which Z represents an iodine atom can be obtained according to J. Med. Chem. 2004, 47(6), 1448.

The product of general formula (II) in which Z represents a bromine atom can be obtained by replacing the iodine atom with a bromine atom in the above method described in J. Med. Chem. 2004, 47(6), 1448.

The product of general formula (II) in which Z represents a benzyloxy radical can be obtained according to the general methods known to those skilled in the art, and in particular by adapting those described in J. Org. Chem. 1967, 32(2), 486.

The product of general formula (II) in which Z represents a hydroxyl radical can be obtained by debenzylation, according to the general methods known to those skilled in the art, of the product of general formula (II) in which z represents a benzyloxy radical.

The product of general formula (II) in which Z represents the trifluoromethanesulphonyloxy radical (also called "triflate" in the rest of the invention) can be obtained by the action of a trifluoromethylsulphonating agent, such as N-phenylbis (trifluoromethanesulphonimide), in an organic solvent such as dichloromethane, in the presence of an organic base such as triethylamine, according to Scheme (2) below.

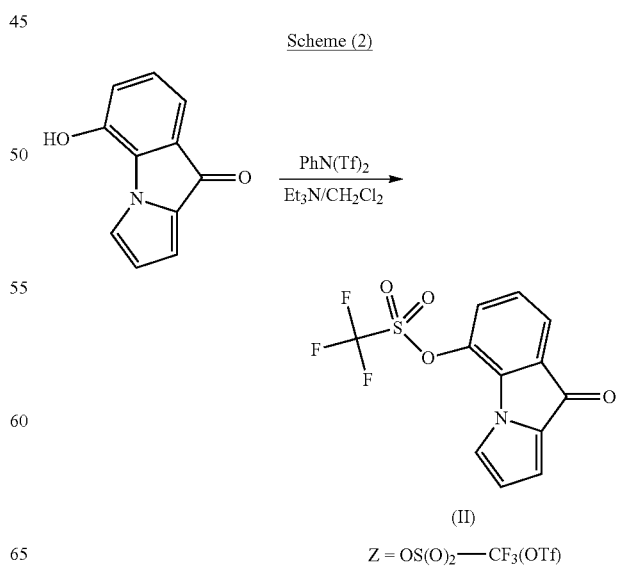

Scheme (2)

Z = OS(O)₂—CF₃(OTf)

The product of general formula (II) in which Z represents a methyl carboxylate radical can be obtained
  either by means of a carbonylation reaction in methanol, catalysed by a palladium complex, such as palladium acetate, in the presence of a phosphine-type ligand such as 1,3-diphenylphosphinopropane,
  or by means of the cyclization reaction with BBr3 in dichloromethane using 2(1-pyrrolyl)isophthalic acid dimethyl ester described in Helv. Chim. Acta 1983, 66(7), 2135,
according to Scheme (3) below:

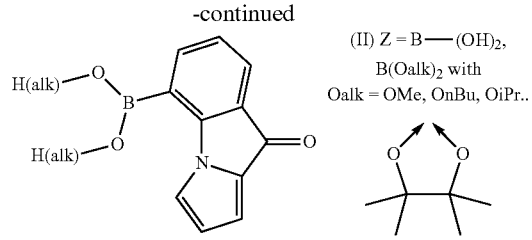

Scheme (3)

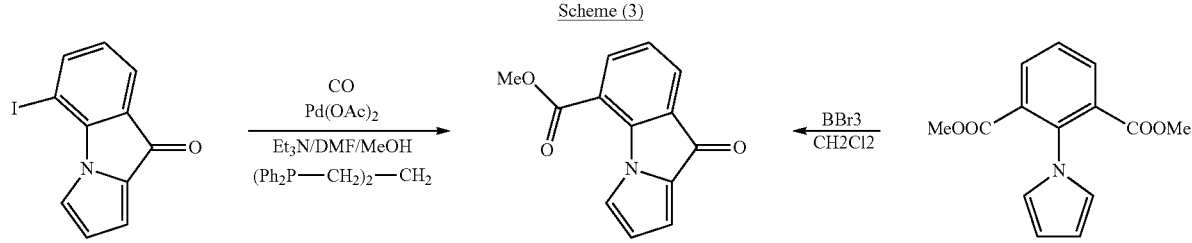

The product of general formula (II) in which Z represents a carboxyl radical can be obtained by hydrolysis, according to the general methods known to those skilled in the art, of the compound of general formula (II) in which z represents a methyl carboxylate radical.

The product of general formula (II) in which Z represents a formyl radical can be obtained by carrying out the process according to the general methods known to those skilled in the art, from the product of general formula (II) in which z represents the methyl carboxylate radical.

The product of general formula (II) in which z represents a chlorocarbonyl radical can be obtained by chloridation of the compound of general formula (II) in which z represents a carboxyl radical according to the general methods known to those skilled in the art.

The products of general formula (II) in which Z represents a boronic acid or a boronic ester, which is optionally cyclic, can be advantageously prepared by the action of a lithium base and then of a borate, such as trimethyl borate, tri-n-butyl borate, triisopropyl borate or pinacolyl diboronate, on 5-bromopyrrolo[1,2-a]indol-9-one at low temperature in an organic solvent such as tetrahydrofuran, or else from 5-iodopyrrolo[1,2-a]indol-9-one or 5-trifluoromethylsulphonyloxypyrrolo[1,2-a]indol-9-one, in the presence of a palladium (0) catalyst, according to Scheme (4).

Scheme 4

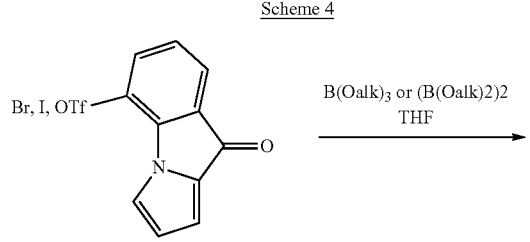

Preparation of the Compounds of General Formula (III)

A subject of the present invention is thus also the methods for synthesizing the products of formula (III), in which, R1 and/or R'1 being as defined above, Het is in the group constituted of:

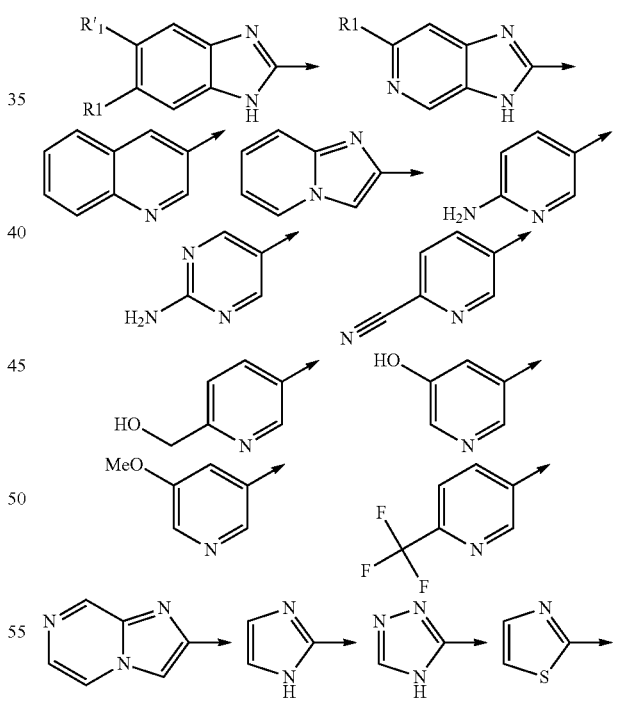

More particularly, when Het does not represent a heterocycle of imidazol-2-yl, triazol-3-yl, benzimidazol-2-yl or azabenzimidazol-2-yl type, and is optionally substituted with one or more radicals R1, as defined above, it is particularly advantageous according to the invention to prepare the compounds of general formula (III)
  either by coupling a compound of general formula (II), in which z represents an iodine atom, a bromine atom or the trifluoromethanesulphonyloxy radical, with a heterocyclic boronic derivative, which may be an acid or an ester, or by coupling a compound of general formula (II), in which z represents a boronic acid or boronic ester, which is optionally cyclic, such as the methyl, n-butyl, isopropyl or pinacol ester, with a bromo or an iodo heterocycle, under the Suzuki reaction conditions, in the presence of a palladium(0) derivative as catalyst, by carrying out the process according to Scheme (5):

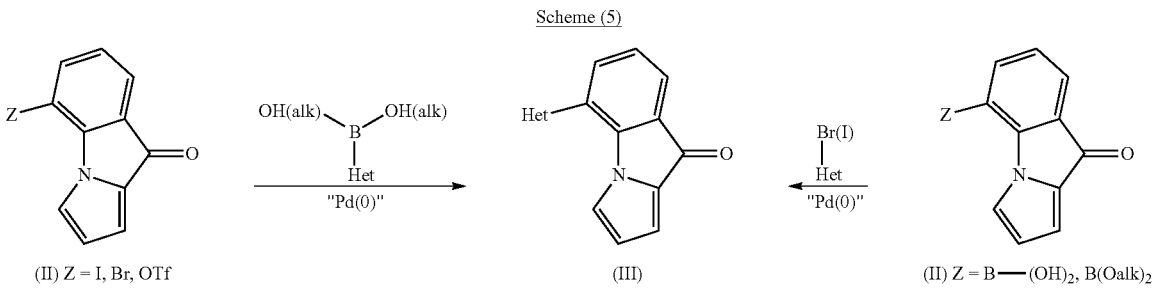

More particularly, when the heterocycle Het is of benzimidazole or azabenzimidazole type—or alternatively of benzoxazole or azabenzoxazole, benzothiazole or azabenzothiazole type, linked via its 2-position to the 5-position of the pyrrolo[1,2-a]indol-9-one, it is particularly advantageous to form said heterocycle by coupling a derivative of ortho-phenylenediamine or of diaminopyridine, or else of ortho-aminophenol, of ortho-aminothiophenol or of aminohydroxypyridine or of aminomercaptopyridine which is ortho-disubstituted, with an acid, an acid chloride, a methyl ester, or an aldehyde, in the 5-position of pyrrolo[1,2-a]indol-9-one by carrying out the process according to Scheme (6):

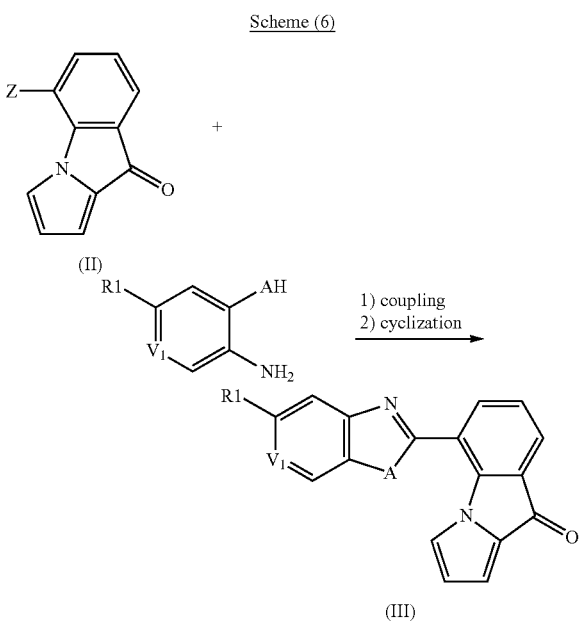

When the 5-carboxylic acid derivative of pyrrolo[1,2-a]indol-9-one is used, it is particularly advantageous to activate this acid using a coupling agent known to those skilled in the art, such as 1-(3-dimethylaminopropyl)-3-ethylcarbodiimide hydrochloride (EDCI) in the presence of 1-hydroxybenzotriazole (HOBT), of O-((ethoxycarbonyl)cyanomethyleneamino)-N,N,N',N'-tetramethyluronium tetrafluoroborate (TOTU) or of O-(1H-benzotriazol-1-yl)-N,N,N',N'-tetramethyluronium hexafluorophosphate (HBTU).

When a pyrrolo[1,2-a]indol-9-one 5-carboxylic acid methyl ester derivative is used, it is advantageous, in the context of the invention, to carry out the process in the presence of trimethylaluminium in a halogenated organic solvent, such as dichloromethane or dichloroethane.

When a 5-carboxaldehyde derivative of pyrrolo[1,2-a]indol-9-one is used, it is advantageous, in the context of the invention, to carry out the process:

either by microwave heating in the presence of silica, according to Tetrahedron Lett. 1998, 39, 4481-84;

or in the presence of dichlorodicyanobenzoquinone (DDQ), according to Tetrahedron 1995, 51, 5813-18;

or in the presence of a mixture of thionyl chloride and of pyridine, according to E.P. 511187;

or in the presence of ferric chloride, according to Eur. J. Med. Chem. 2006, 31, 635-42.

Various conditions for cyclization of the mixture of intermediate amides can be used in the context of the invention, such as acetic acid or a mixture of trifluoroacetic acid and trifluoroacetic anhydride. It is also particularly advantageous, in the context of the invention, to carry out this type of thermal cyclization in an acidic medium by heating in a microwave reactor.

More particularly, when said heterocycle is of imidazole, oxazole or thiazole type, linked via its 2-position to the 5-position of the pyrrolo[1,2-a]indol-9-one, it is particularly advantageous to form said heterocycle using an acid, an acid chloride, an ester or an aldehyde in the 5-position of the pyrrolo[1,2-a]indol-9-one, by carrying out the process according to Scheme (7):

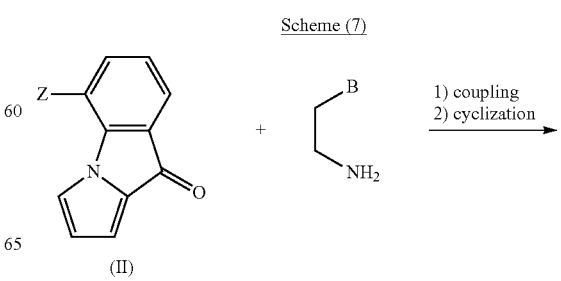

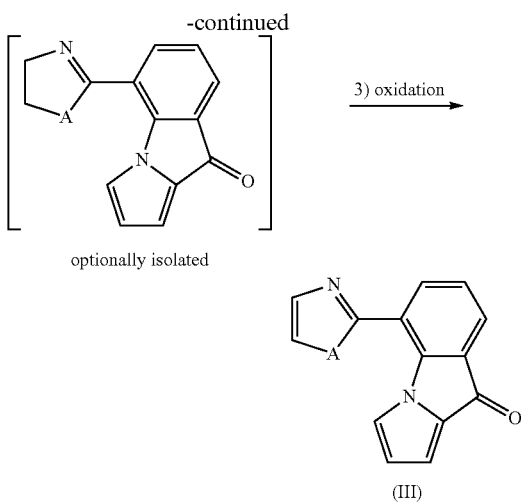

optionally isolated (III)

A = NH, O, S
B = AH or a reactive group which is a precursor of A
Z = COOH, COCl, COOMe, CHO In the context of the invention, it is particularly advantageous to carry out the process:

1. in the case where said heterocycle is an imidazole or an imidazoline:
   using a 2-azidoethylamine, according to Tetrahedron, 47(38), 1991, 8177-94,
   using an ethylenediamine, according to Biorg. Med. Chem. Lett. 12(3), 2002, 471-75,
   using glyoxal and aqueous ammonia, according to J. Med. Chem., 46(25), 2003, 5416-27;

2. in the case where said heterocycle is an oxazole or an oxazoline:
   using a 2-azidoethanol, according to J. Org. Chem., 61(7), 1996, 2487-96,
   using a 2-aminoethanol, according to J. Med. Chem. 47(8), 2004, 1969-86 or Khim. Geterosikl. Soed. 1984(7), 881-4,
   using 2-aminoacetaldehyde diethylacetal, according to Heterocycles, 39(2), 1994, 767-78;

3. in the case where said heterocycle is a thiazole or a thiazoline:
   using a 2-chloroethylamine and Lawesson's reagent, according to Helv. Chim. Acta, 88(2), 2005, 187-95,
   using a 2-aminoethanethiol, according to J. Org. Chem. 69(3), 2004, 811-4, or Tetrahedron Lett., 41(18), 2000, 3381-4.

More generally, it is advantageous, in the context of the invention, to form the heterocycle of a product of general formula (III) using a triflate, a brominated or iodinated derivative, a boronic acid or ester, a carboxylic acid, an acid chloride of an ester of a carboxylic acid, or an aldehyde, in the 5-position of the pyrrolo[1,2-a]indol-9-one, by any one of the methods of synthesis known to those skilled in the art, such as those described in Comprehensive Organic Chemistry, by D. H. R. Barton et al. (Pergamon Press) or Advances in Heterocyclic Chemistry (Academic Press) or Heterocyclic Compounds (Wiley Intersciences).

Preparation of the Compounds of General Formula (IV)

A subject of the present invention is also the methods for synthesizing the products of formula (IV), in which Z represents a carboxylic ester group, in particular methyl ester, a benzyloxy radical, an iodine atom, a bromine atom, a triflate radical, a boronic acid or a boronic ester, a carboxylic acid, a carboxaldehyde or a hydroxyl radical.

The products of general formula (IV) in which Z represents a carboxylic ester, a benzyloxy radical, an iodine atom, a bromine atom, a triflate radical, a boronic acid or a boronic ester, a carboxylic acid, a carboxaldehyde or a hydroxyl radical can be advantageously prepared in the context of the invention by reacting a product of general formula (II), in which Z represents a carboxylic ester, a benzyloxy radical, an iodine atom or a bromine atom according to the general methods known to those skilled in the art, in particular those described in Comprehensive Organic Chemistry, by D. Barton et al. (Pergamon Press), Advanced Organic Chemistry, by J. March (Wiley Interscience) or Compendium of Organic Synthetic Methods (Wiley Interscience). It is particularly advantageous to use the method described in scheme (8):

Scheme (8)

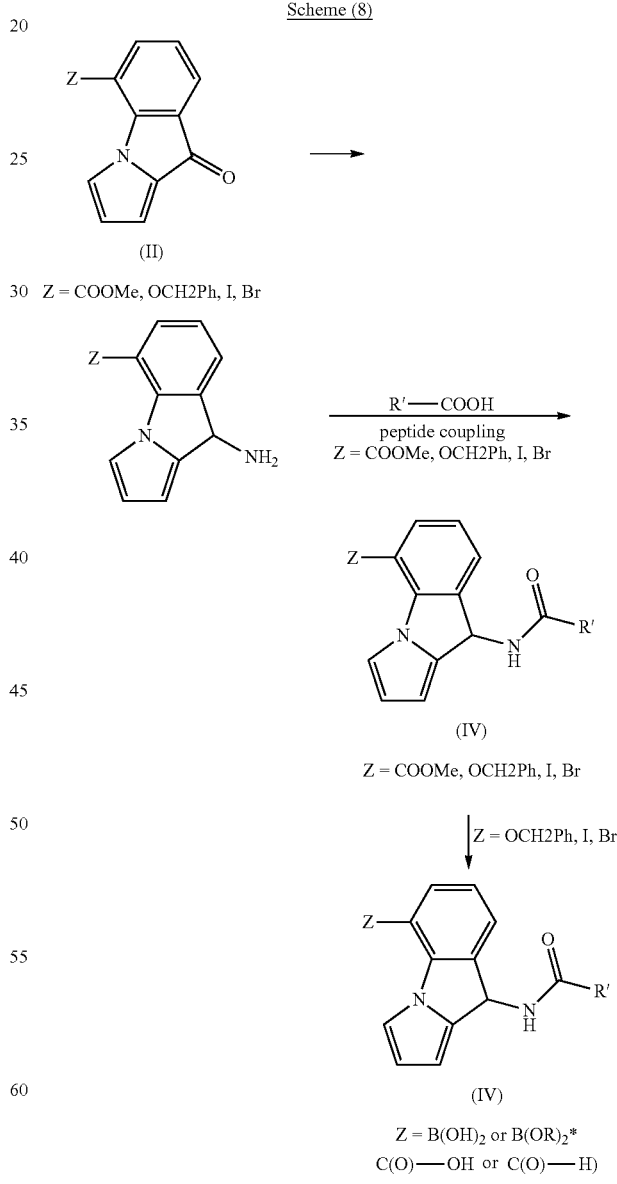

Preparation of the Compounds of General Formula (I)

Method A Using the Compounds (III):

A subject of the present invention is also the methods for synthesizing the products of formula (I), from the compounds of general formula (III), which can be carried out according to the general methods known to those skilled in the art, in particular those described in Comprehensive Organic Chemistry, by D. Barton et al. (Pergamon Press), Advanced Organic Chemistry, by J. March (Wiley Interscience) or Compendium of Organic Synthetic Methods (Wiley Interscience). It is particularly advantageous to use the method of scheme (9):

either by coupling a compound of general formula (IV), in which z represents an iodine atom, a bromine atom or the trifluoromethanesulphonyloxy radical, with a heterocyclic boronic derivative, which may be an acid or an ester, or by coupling a compound of general formula (IV), in which z represents a boronic acid or a boronic ester, which is optionally cyclic, such as the methyl, n-butyl, isopropyl or pinacol ester, with a bromo or an iodo heterocycle, under the Suzuki reaction conditions, in the presence of a palladium(0) derivative as catalyst, by carrying out the process according to scheme (10):

Scheme (10)

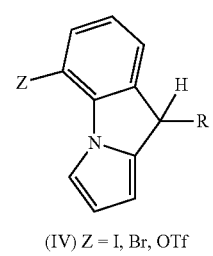 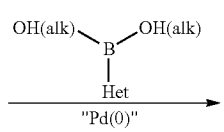 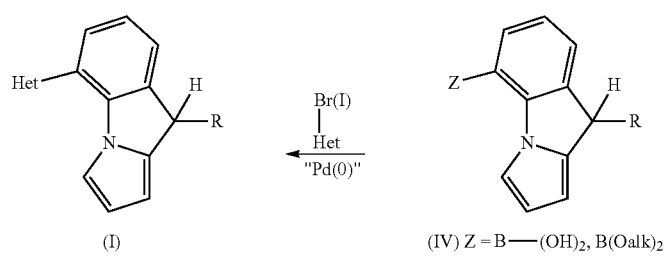

(IV) Z = I, Br, OTf        (I)        (IV) Z = B—(OH)$_2$, B(Oalk)$_2$

More particularly, when the heterocycle Het is of benzimidazole or azabenzimidazole type, or alternatively of benzoxazole or azabenzoxazole type, or benzothiazole or azabenzothiazole type, linked via its 2-position to the 5-position of the pyrrolo-[1,2-a]indole, it is particularly advantageous to form said heterocycle by coupling a derivative of ortho-phenylenediamine or of diaminopyridine, or else of ortho-aminophenol, of ortho-aminothiophenol, or of aminohydroxypyridine or of aminomercaptopyridine which is ortho-disubstituted, with an acid, an acid chloride, a methyl ester, or a carboxaldehyde in the 5-position of pyrrolo[1,2-a]indole by carrying out the process according to Scheme (11):

Scheme (9)

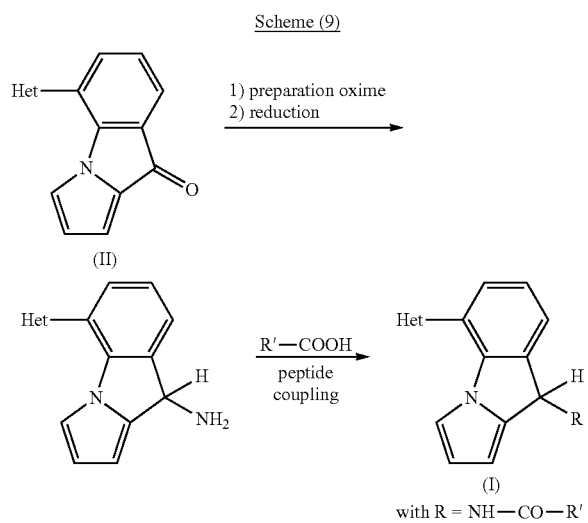

with R = NH—CO—R'

Method B Using the Compounds (IV):

A subject of the present invention is also the methods for synthesizing the products of formula (I), from the compounds of general formula (IV), which can be carried out according to the general methods known to those skilled in the art, in particular those described in Comprehensive Organic Chemistry, by D. Barton et al. (Pergamon Press), Advanced Organic Chemistry, by J. March (Wiley Interscience) or Compendium of Organic Synthetic Methods (Wiley Interscience).

When Het does not represent a heterocycle of imidazol-2-yl, triazol-3-yl, benzimidazol-2-yl or azabenzimidazol-2-yl type, and is optionally substituted with one or more R1 radicals, as defined above, it is particularly advantageous according to the invention to prepare the compounds of general formula (I)

Scheme (11)

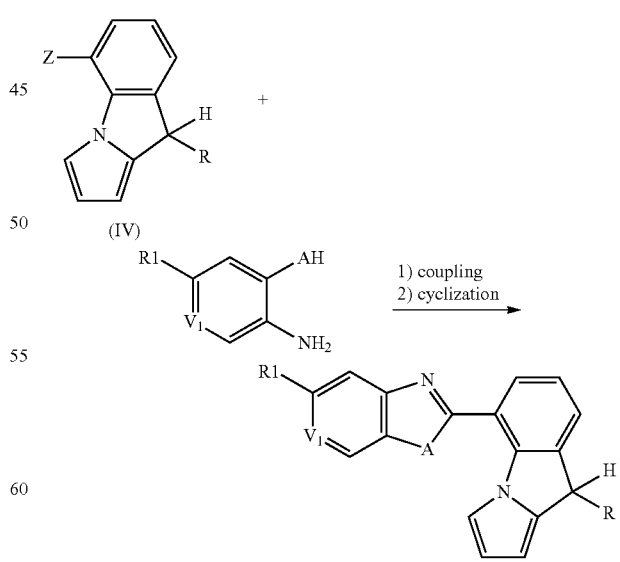

A = NH, O, S
Z = COOH, COOMe, CHO
V1 = N, CR1
R1 as defined above

When the 5-carboxylic acid derivative of pyrrolo[1,2-a]indole is used, it is particularly advantageous to activate this acid using a coupling agent known to those skilled in the art, such as 1-(3-dimethylaminopropyl)-3-ethylcarbodiimide hydrochloride (EDCI) in the presence of 1-hydroxybenzotriazole (HOBT), of O-((ethoxycarbonyl)cyanomethyleneamino)-N, N,N',N'-tetramethyluronium tetrafluoroborate (TOTU) or of O-(1H-benzotriazol-1-yl)-N,N,N',N'-tetramethyluronium hexafluorophosphate (HBTU).

When a pyrrolo[1,2-a]indole 5-carboxylic acid methyl ester derivative is used, it is advantageous, in the context of the invention, to carry out the process in the presence of trimethylaluminium in a halogenated organic solvent, such as dichloromethane or dichloroethane.

When a 5-carboxaldehyde derivative of pyrrolo[1,2-a]indole is used, it is advantageous, in the context of the invention, to carry out the process:

- either by microwave heating in the presence of silica, according to Tetrahedron Lett. 1998, 39, 4481-84;
- or in the presence of dichlorodicyanobenzoquinone (DDQ), according to Tetrahedron 1995, 51, 5813-18;
- or in the presence of a mixture of thionyl chloride and pyridine, according to E.P. 511187;
- or in the presence of ferric chloride, according to Eur. J. Med. Chem. 2006, 31, 635-42.

Various conditions for cyclization of the mixture of intermediate amides can be used in the context of the invention, such as acetic acid or a mixture of trifluoroacetic acid and trifluoroacetic anhydride. It is also particularly advantageous, in the context of the invention, to carry out this type of thermal cyclization in an acidic medium by heating in a microwave reactor.

More particularly, when said heterocycle is of the type imidazole, oxazole or thiazole, linked via its 2-position to the 5-position of the pyrrolo[1,2-a]indole, it is particularly advantageous to form said heterocycle using an acid, an ester or an aldehyde in the 5-position of the pyrrolo[1,2-a]indole, by carrying out the process according to Scheme (12):

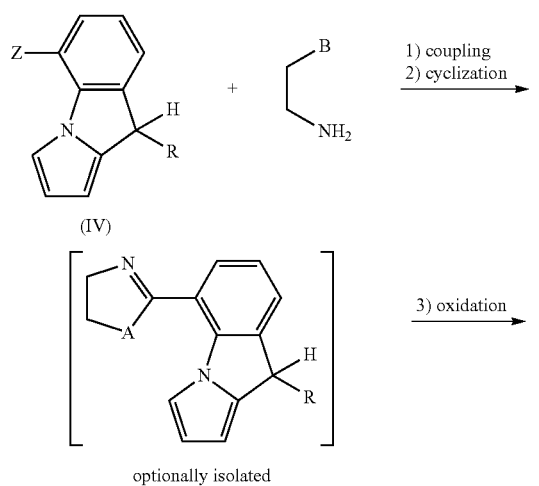

Scheme (12)

optionally isolated

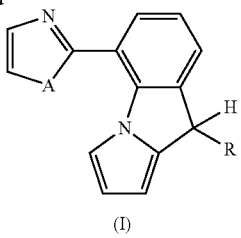

(I)

A = NH, O, S
B = AH or a reactive group which is a precursor of A
Z = COOH, COOMe, CHO In the context of the invention it is particularly advantageous to carry out the process:

4. in the case where said heterocycle is an imidazole or an imidazoline:
   - using a 2-azidoethylamine, according to Tetrahedron, 47(38), 1991, 8177-94,
   - using an ethylenediamine, according to Biorg. Med. Chem. Lett. 12(3), 2002, 471-75,
   - using glyoxal and aqueous ammonia, according to J. Med. Chem., 46(25), 2003, 5416-27;

5. in the case where said heterocycle is an oxazole or an oxazoline:
   - using a 2-azidoethanol, according to J. Org. Chem., 61(7), 1996, 2487-96,
   - using a 2-aminoethanol, according to J. Med. Chem. 47(8), 2004, 1969-86 or Khim. Geterosikl. Soed. 1984(7), 881-4,
   - using 2-aminoacetaldehyde diethylacetal, according to Heterocycles, 39(2), 1994, 767-78;

6. in the case where said heterocycle is a thiazole or a thiazoline:
   - using a 2-chloroethylamine and Lawesson's reagent, according to Helv. Chim. Acta, 88(2), 2005, 187-95,
   - using a 2-aminoethanethiol, according to J. Org. Chem. 69(3), 2004, 811-4, or Tetrahedron Lett., 41(18), 2000, 3381-4.

More generally, it is advantageous, in the context of the invention, to form the heterocycle of a product of general formula (IV) using a triflate, a brominated or iodinated derivative, a boronic acid or a boronic ester, a carboxylic acid, a carboxylic acid ester or an aldehyde, in the 5-position of the pyrrolo[1,2-a]indole, by any one of the methods of synthesis known to those skilled in the art, such as those described in Comprehensive Organic Chemistry, by D. H. R. Barton et al. (Pergamon Press) or Advances in Heterocyclic Chemistry (Academic Press) or Heterocyclic Compounds (Wiley Intersciences).

A subject of the present invention is thus also, as novel industrial products, the synthesis intermediates of formulae (II), (III) and (IV):

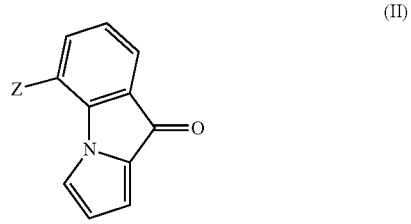

(II)

-continued

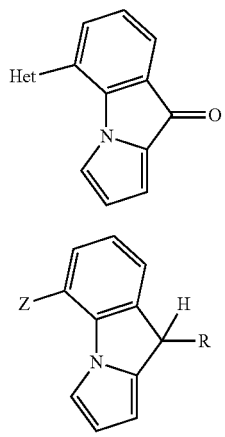

(III)

(IV)

Z = OTf, I, Br, B(OH)₂ or B(OR)₂* or
C(O)—OMe, C(O)—OH or C(O)—H or
OH or O—CH₂—Ph
*B(OR)₂ being able to form a ring in which compounds of formulae (II), (III) and (IV) as defined above, the substituents Het and R have the meanings indicated above for the products of formula (I) and z has the meaning indicated above, with the exception of the compound of formula (II) in which z represents an iodine atom.

The products which are subjects of the present invention have advantageous pharmacological properties: it has been observed that they in particular possess inhibitory properties on the activities of chaperone proteins, and in particular on their ATPase activities.

Among these chaperone proteins, mention is in particular made of the human chaperone HSP90.

The products corresponding to general formula (I) as defined above thus have a considerable inhibitory activity on the Hsp90 chaperone.

Tests given in the experimental section hereinafter illustrate the inhibitory activity of products of the present invention with respect to such chaperone proteins.

These properties thus mean that the products of general formula (I) of the present invention can be used as medicaments in the treatment of malignant tumours.

The products of formula (I) can also be used in the veterinary field.

A subject of the invention is therefore the use, as medicaments, of the products of formula (I) as defined above.

A subject of the invention is in particular the use, as medicaments, of the products of formula (I) as defined above, the names of which are given below:
1H-pyrrolo[2,3-b]pyridine-4-carboxylic acid [5-(6-fluoro-1H-benz-imidazol-2-yl)-9H-pyrrolo[1,2-a]indol-9-yl] amide,
1H-pyrrolo[2,3-b]pyridine-4-carboxylic acid (5-quinolin-3-yl-9H-pyrrolo[1,2-a]indol-9-yl)amide,
1H-pyrrolo[2,3-b]pyridine-4-carboxylic acid [5-(3H-imidazo[4,5-c]pyridin-2-yl)-9H-pyrrolo[1,2-a]indol-9-yl] amide,
6-chloro-1H-pyrrolo[2,3-b]pyridine-4-carboxylic acid [5-(3H-imidazo[4,5-c]pyridin-2-yl)-9H-pyrrolo[1,2-a]indol-9-yl]amide,
and also the pharmaceutically acceptable addition salts with inorganic and organic acids or with inorganic and organic bases of said products of formula (I).

A subject of the invention is in particular, as medicaments, products of formula (I) as defined above:

Het is chosen from the group constituted of:

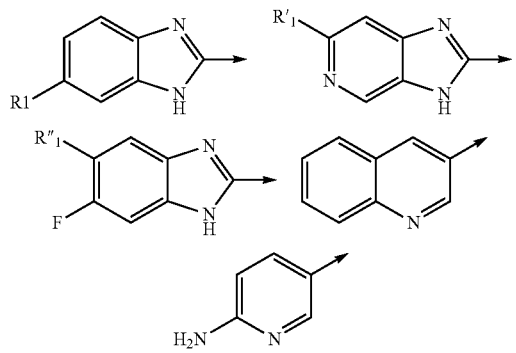

with:
R1 represents H, F, Cl, Br, CF₃, NO₂, CN, CH₃, OH, OCH₃, OCF₃, CO₂Me, CONH₂, CONHMe, CONH—(CH₂)₃—OMe, CONH—(CH₂)₃—N(Me)₂, NHC(O)Me, SO₂NH₂ or SO₂N(Me)₂;
R'1 represents H, CONH₂, CONHMe or OMe;
R"1 represents F, Cl, OH, OMe, CN, O—(CH₂)₃—OMe or O—(CH₂)₃—N(Me)₂;
and R is chosen from the group constituted of:

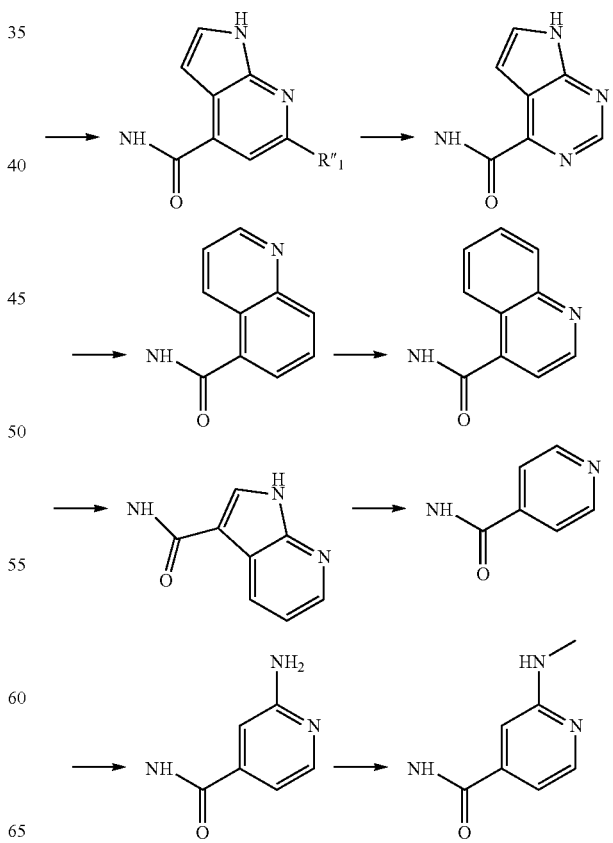

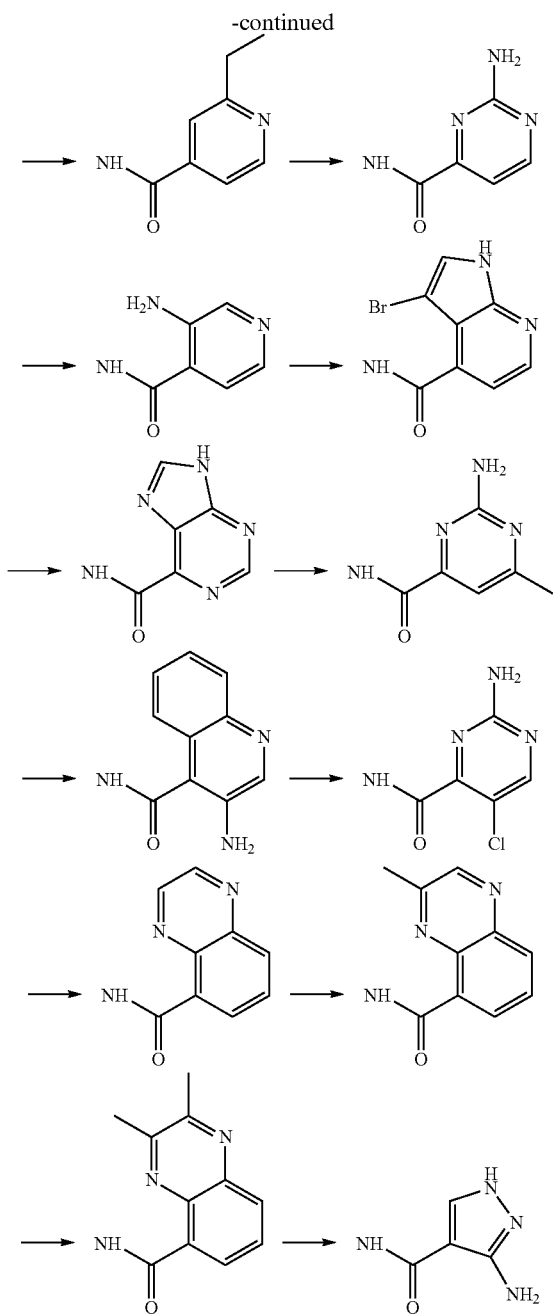

and also the prodrugs thereof, said products of formula (I) being in all the possible isomeric forms: tautomeric, racemic, enantiomeric and diastereoisomeric, and also the pharmaceutically acceptable addition salts with inorganic and organic acids or with inorganic and organic bases of said products of formula (I).

The products can be administered parenterally, orally, perlingually or topically.

A subject of the invention is also pharmaceutical compositions, characterized in that they contain, as active ingredient, at least one of the medicaments of general formula (I).

These compositions can be provided in the form of injectable solutions or suspensions, tablets, coated tablets, capsules, syrups, creams, ointments and lotions. These pharmaceutical forms are prepared according to the usual methods. The active ingredient can be incorporated into excipients normally used in these compositions, such as aqueous or nonaqueous carriers, talc, gum arabic, lactose, starch, magnesium stearate, fatty substances of animal or plant origin, paraffin derivatives, glycols, various wetting agents, dispersants or emulsifiers, or preserving agents.

The usual dose, which can vary according to the individual treated and the condition in question, can be, for example, from 10 mg to 1 g per day in humans, orally.

The present invention thus relates to the use of products of formula (I) as defined above or of pharmaceutically acceptable salts of said products of formula (I), for the preparation of medicaments for inhibiting the activity of chaperone proteins, and in particular of Hsp90.

The present invention thus relates in particular to the use of products of formula (I) as defined above or of pharmaceutically acceptable salts of said products of formula (I), in which the chaperone protein is Hsp90.

The present invention thus relates to the use of products of formula (I) as defined above or of pharmaceutically acceptable salts of said products of formula (I), for the preparation of a medicament for preventing or treating a disease characterized by a disturbance of the activity of a chaperone protein of Hsp90 type, and in particular such a disease in a mammal.

The present invention relates to the use of products of formula (I) as defined above or of pharmaceutically acceptable salts of said products of formula (I), for the preparation of a medicament for preventing or treating a disease belonging to the following group: neurodegenerative diseases such as Huntington's disease, Parkinson's disease, focal cerebral ischaemia, Alzheimer's disease, multiple sclerosis and amyotrophic lateral sclerosis, malaria, Brugia filariasis, Bancroft's filariasis, toxoplasmosis, treatment-resistant mycoses, hepatitis B, hepatitis C, the herpes virus, dengue (or tropical flu), spinal and bulbar muscular atrophy, mesangial cell proliferation disorders, thromboses, retinopathies, psoriasis, muscle degeneration, diseases in oncology, and cancers.

The present invention thus relates to the use of products of formula (I) as defined above or of pharmaceutically acceptable salts of said products of formula (I), for the preparation of a medicament for treating diseases in oncology.

The present invention relates in particular to the use of products of formula (I) as defined above or of pharmaceutically acceptable salts of said products of formula (I), for the preparation of a medicament for treating cancers.

Among these cancers, the present invention focuses most particularly on the treatment of solid tumours and on the treatment of cancers resistant to cytotoxic agents.

The present invention thus relates in particular to the use of products of formula (I) as defined in any one of the preceding claims or of pharmaceutically acceptable salts of said products of formula (I), for the preparation of a medicament for treating cancers, among which are lung cancer, breast cancer and ovarian cancer, glioblastomas, chronic myeloid leukaemias, acute lymphoblastic leukaemias, prostate cancer, pancreatic cancer and colon cancer, metastatic melanomas, thyroid tumours and renal carcinomas.

Thus, among the main potential indications of Hsp90 inhibitors, mention may, by way of nonlimiting example, be made of:

"non small cell" lung cancers, breast cancers, ovarian cancers and glioblastomas which overexpress EGF-R or HER2;
chronic myeloid leukaemias which overexpress Bcr-Abl;
acute lymphoblastic leukaemias which overexpress Flt-3;
breast, prostate, lung, pancreatic, colon or ovarian cancers which overexpress Akt;

metastatic melanomas and thyroid tumours which overexpress the mutated form of the B-Raf protein;
androgen-dependent and androgen-independent prostate cancers;
oestrogen-dependent and oestrogen-independent breast cancers;
renal carcinomas which overexpress HIF-1a or the mutated c-met protein.

The present invention focuses even more particularly on the treatment of breast cancer, colon cancer and lung cancer.

The present invention also relates to the use of products of formula (I) as defined above or of pharmaceutically acceptable salts of said products of formula (I), for the preparation of a medicament for use in cancer chemotherapy.

As medicaments according to the present invention for use in cancer chemotherapy, the products of formula (I) according to the present invention can be used alone or in combination with chemotherapy or radiotherapy, or alternatively in combination with other therapeutic agents.

The present invention thus relates in particular to the pharmaceutical compositions as defined above containing, in addition to the active ingredients, other medicaments for anticancer chemotherapy.

Such therapeutic agents can be commonly used anti-tumour agents.

As examples of known protein kinase inhibitors, mention may in particular be made of butyrolactone, flavopiridol, 2-(2-hydroxyethylamino)-6-benzylamino-9-methylpurine, olomucine, Glivec and Iressa.

The products of formula (I) according to the present invention may thus also be advantageously used in combination with anti-proliferative agents: by way of examples of such anti-proliferative agents, but without however being limited to this list, mention may be made of aromatase inhibitors, anti-oestrogens, topoisomerase inhibitors, agents that are active on microtubules, alkylating agents, histone deacetylase inhibitors, farnesyl transferase inhibitors, COX-2 inhibitors, MMP inhibitors, mTOR inhibitors, antineoplastic antimetabolites, platinum compounds, proteasome inhibitors, inhibitors of Histone Deactylase (HDACs), and in particular inhibitors of HDAC6, compounds which bring about a reduction in protein kinase activity and also anti-angiogenic compounds, gonadorelin agonists and anti-androgens.

The present invention therefore relates to products of formula (I) as Hsp90 chaperone inhibitors, said products of formula (I) being in all the possible isomeric forms: tautomeric, racemic, enantiomeric and diastereoisomeric, and also the pharmaceutically acceptable addition salts with inorganic and organic acids or with inorganic and organic bases of said products of formula (I), and the prodrugs thereof.

The present invention relates in particular to products of formula (I) as defined above, as Hsp90 inhibitors.

The products of formula (I) according to the present invention can be prepared by application or adaptation of known methods, and in particular of the methods described in the literature, for instance those described by R. C. Larock in: Comprehensive Organic Transformations, VCH publishers, 1989.

In the reactions described hereinafter, it may be necessary to protect reactive functional groups such as, for example, hydroxyl, amino, imino, thio or carboxyl groups, when the latter are desired in the final product but when their participation is not desired in the reactions for synthesizing the products of formula (I). Conventional protective groups can be used in accordance with the usual standard practices, such as those described, for example, by T. W. Greene and P. G. M. Wuts in "Protective Groups in Organic Chemistry" John Wiley and Sons, 1991.

The experimental section hereinafter gives non-limiting examples of starting products: other starting products can be found commercially or can be prepared according to the usual methods known to those skilled in the art.

EXAMPLES ILLUSTRATING THE INVENTION

The examples of which the preparation follows illustrate the present invention without, however, limiting it.

All the examples described were characterized by proton NMR spectroscopy and by mass spectroscopy, the majority of these examples were also characterized by infrared spectroscopy.

Unless different conditions are specifically described, the LC/MS mass spectra, reported in the description of the various examples below, were carried out under the following liquid chromatography conditions:

Method A:
The spectra were obtained on a Waters ZQ machine
Ionization: positive and/or negative mode electrospray (ES+/−)
Chromatographic conditions:
  Column: XBridge $C_{18}$ 2.5 μm 3×50 mm
  Solvents: A: $H_2O$ (0.1% formic acid)
    B: $CH_3CN$ (0.1% formic acid)
  Column temperature: 70° C.
  Flow rate: 0.9 ml/min
  Gradient (7 min): from 5 to 100% of B in 5.3 min; 5.5 min: 100% of B; 6.3 min: 5% of B Method B:
The spectra were obtained on a WATERS QUATTRO PREMIER machine
Ionization: positive and/or negative mode electrospray (ES+/−)
Chromatographic conditions:
  Column: ACQUITY BEH $C_{18}$ 1.7 μm 2.1×50 mm
  Solvents: A: $H_2O$ (0.1% formic acid)
    B: $CH_3CN$ (0.1% formic acid)
  Column temperature: 70° C.
  Flow rate: 0.7 ml/min
  Gradient: (3.7 min): from 5 to 100% of B in 3 min; 3.6 min: 5% of B Method C:
The spectra were obtained on a WATERS QUATTRO PREMIER machine
Ionization: positive and/or negative mode electrospray (ES+/−)
Chromatographic conditions:
  Column: ACQUITY BEH $C_{18}$ 1.7 μm-2.1×50 mm
  Solvents: A: $H_2O$ (0.1% formic acid)
    B: $CH_3CN$ (0.1% formic acid)
  Column temperature: 70° C.
  Flow rate: 0.7 ml/min
  Gradient (6 min): from 5 to 100% of B in 5 min; 5.5 min: 5% of B Method D
The spectra were obtained on a WATERS UPLC-SQD machine
Ionization: positive and/or negative mode electrospray (ES+/−)
Chromatographic conditions:
  Column: ACQUITY BEH $C_{18}$ 1.7 μm-2.1×50 mm
  Solvents: A: $H_2O$ (0.1% formic acid)
    B: $CH_3CN$ (0.1% formic acid)

Column temperature: 50° C.
Flow rate: 1 ml/min
Gradient (2 min): from 5 to 50% of B in 0.8 min; 1.2 min: 100% of B; 1.85 min: 100% of B; 1.95: 5% of B Example 1

Synthesis of 1H-pyrrolo[2,3-b]pyridine-4-carboxylic acid [5-(6-fluoro-1H-benzimidazol-2-yl)-9H-pyrrolo[1,2-a]indol-9-yl]amide

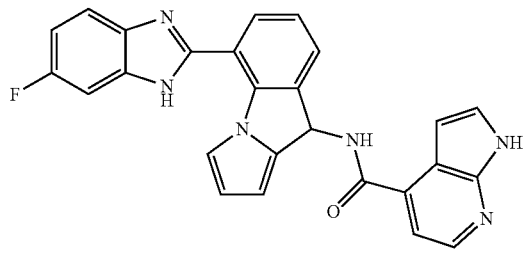

Stage 1:
Method 1: A mixture of 1.00 g of 5-iodopyrrolo[1,2-a]indol-9-one (which can be prepared according to J. Med. Chem. 2004, 47(6), 1448), 152 mg of palladium acetate, 280 mg of 1,3-diphenylphosphinopropane and 0.47 ml of triethylamine in 6 ml of methanol and 15 ml of dimethylformamide is maintained at 50° C. for 16 hours under a 2 bar carbon monoxide pressure, in an autoclave. After flushing with argon, the reaction medium is filtered, the insoluble material being washed with methanol, and then the filtrate is evaporated to dryness. The orangey-brown residue is chromatographed on silica gel (40-65 µm), elution being carried out with dichloromethane. 800 mg of 9-oxo-9H-pyrrolo[1,2-a]indole-5-carboxylic acid methyl ester are obtained in the form of a beige solid, the characteristics of which are the following:
1H NMR spectrum (400 MHz, δ in ppm, DMSO-d6): 3.95 (s, 3H); 6.43 (dd, J=3.8 and 2.7 Hz, 1H); 6.98 (dd, J=3.8 and 1.0 Hz, 1H); 7.33 (t, J=7.5 Hz, 1H); 7.78 (dd, J=7.5 and 1.4 Hz, 1H); 7.97 to 8.03 (m, 2H).
Mass spectrum (LC/MS Method A): Retention time Tr (min)=3.48; [M+H]+: m/z 228.

Method 2: In a 50 ml round-bottomed flask, 3 ml of a 1M solution of boron tribromide in dichloromethane are added, at ambient temperature, to a mixture of 260 mg of 2-pyrrol-1-ylisophthalic acid dimethyl ester (which can be prepared according to Helvetica Chim. Acta 1983, 66(7), 2135) dissolved in 4 ml of dichloromethane. The reaction medium is stirred at ambient temperature for 2 hours and then 5 ml of water are added. After separation by settling out, the aqueous phase is re-extracted with twice 15 ml of dichloromethane. The combined organic phases are washed with twice 20 ml of water, dried over magnesium sulphate, and evaporated to dryness under vacuum. The residue is chromatographed on silica gel (15-40 µm), elution being carried out with a mixture of dichloromethane and cyclohexane (50/50 v/v). 122 mg of 9-oxo-9H-pyrrolo[1,2-a]indole-5-carboxylic acid methyl ester are obtained in the form of a yellowish solid, the characteristics of which are identical to those of the product obtained by method 1.

Stage 2:
In a 250 ml round-bottomed flask, a mixture of 800 mg of 9-oxo-9H-pyrrolo[1,2-a]indole-5-carboxylic acid methyl ester obtained according to the preceding stage and of 740 mg of lithium hydroxide monohydrate in 25 ml of water and 100 ml of methanol is refluxed for 3 hours. The reaction medium is evaporated to dryness under vacuum, and the solid is taken up in 35 ml of water and brought to pH 3 with 5M hydrochloric acid. A precipitate appears and the medium is extracted with 3 times 35 ml of a mixture of dichloromethane and methanol (95/5 v/v). The combined organic extracts are washed with 3 times 15 ml of water, dried over magnesium sulphate, and evaporated to dryness under vacuum. 630 mg of 9-oxo-9H-pyrrolo[1,2-a]indole-5-carboxylic acid are obtained in the form of a beige solid, the characteristics of which are the following:
Mass spectrum (LC/MS Method A): Retention time Tr (min)=2.69; [M+H]+: m/z 214; [M−H]−: m/z 212.

Stage 3:
In a 250 ml round-bottomed flask under argon, a mixture of 620 mg of 9-oxo-9H-pyrrolo[1,2-a]indole-5-carboxylic acid obtained according to the preceding stage, 1.50 g of o-(1H-benzotriazol-1-yl)-N,N,N',N'-tetramethyluronium hexafluorophosphate (HBTU) and 0.44 ml of diisopropylethylamine in 55 ml of tetrahydrofuran is stirred at ambient temperature for 1 hour. 367 mg of 4-fluoro-o-phenylenediamine are then added and the stirring is maintained for 3 days. The reaction medium is evaporated to dryness under vacuum and the residue is taken up with 15 ml of a mixture of dichloromethane and methanol (90/10 v/v). The organic phase is washed with 10 ml of a saturated solution of sodium bicarbonate, then with 3 times 5 ml of distilled water, and dried over magnesium sulphate. After evaporation to dryness under vacuum, the residue is loaded as a dry spot onto a column of silica gel (40-63 µm) and chromatographed, elution being carried out with a mixture of dichloromethane and methanol (95/5 v/v). 379 mg of 9-oxo-9H-pyrrolo[1,2-a]indole-5-carboxylic acid (2-amino-4-fluorophenyl)amide are obtained in the form of a beige solid, the characteristics of which are the following:
1N NMR spectrum (400 MHz, δ in ppm, DMSO-d6): 5.38 (broad s, 2H); 6.35 (dd, J=3.5 and 2.5 Hz, 1H); 6.39 (td, J=8.6 and 2.9 Hz, 1H); 6.55 (dd, J=11.2 and 2.9 Hz, 1H); 6.92 (broad d, J=3.5 Hz, 1H); 7.22 (dd, J=8.6 and 6.4 Hz, 1H); 7.33 (t, J=7.6 Hz, 1H); 7.57 (broad d, J=2.5 Hz, 1H); 7.68 (broad d, J=7.6 Hz, 1H); 7.94 (broad d, J=7.6 Hz, 1H); 9.91 (s, 1H).
Mass spectrum (LC/MS Method A): Retention time Tr (min)=3.10; [M+H]+: m/z 322; [M−H]−: m/z 320.

Stage 4:
In a 250 ml round-bottomed flask, a mixture of 375 mg of 9-oxo-9H-pyrrolo[1,2-a]indole-5-carboxylic acid (2-amino-4-fluorophenyl)amide obtained according to the preceding stage, in 40 ml of glacial acetic acid, is refluxed for 3 hours. The reaction medium is evaporated to dryness under vacuum and the residue is chromatographed on silica gel (15-40 µm), elution being carried out with a gradient of methanol (0 to 30% by volume) in dichloromethane. 119 mg of 5-(6-fluoro-1H-benzimidazol-2-yl)pyrrolo[1,2-a]indol-9-one are obtained in the form of a yellowish solid, the characteristics of which are the following:
1H NMR spectrum (400 MHz, δ in ppm, DMSO-d6): 6.36 (dd, J=3.9 and 2.9 Hz, 1H); 6.96 (dd, J=3.9 and 1.0 Hz, 1H); 7.16 (td, J=9.5 and 2.4 Hz, 1H); 7.42 (t, J=7.6 Hz, 1H); 7.50 (broad d, J=9.5 Hz, 1H); 7.69 (dd, J=7.6 and 1.0 Hz, 1H); 7.72 (m partially masked, 1H); 7.99 (dd, J=7.6 and 1.0 Hz, 1H); 8.45 (dd, J=2.9 and 1.0 Hz, 1H); 13.30 (broad m, 1H).
Mass spectrum (LC/MS Method B): Retention time Tr (min)=1.83; [M+H]+: m/z 304; [M−H]−: m/z 302.

Stage 5:
In a 20 ml round-bottomed flask, a mixture of 60 mg of 5-(6-fluoro-1H-benzimidazol-2-yl)pyrrolo[1,2-a]indol-9- one obtained according to the preceding stage and 42 mg of hydroxylamine hydrochloride in 5 ml of pyridine is brought to reflux for 6 hours. The reaction medium is evaporated to dryness under vacuum and the residue taken up with 25 ml of a saturated solution of sodium bicarbonate is extracted with 3 times 25 ml of ethyl acetate. The combined organic phases are washed with 25 ml of a saturated solution of sodium chloride, dried over magnesium sulphate, and evaporated to dryness under vacuum. 97 mg of 5-(6-fluoro-1H-benzimidazol-2-yl) pyrrolo[1,2-a]indol-9-one oxime are obtained in the form of a yellowish oil, the characteristics of which are the following:

1H NMR spectrum (400 MHz, δ in ppm, DMSO-d6): 6.34 (dd, J=3.4 and 2.9 Hz, 1H); 6.78 (dd, J=3.4 and 1.0 Hz, 1H); 7.14 (td, J=10.5 and 3.0 Hz, 1H); 7.37 (t, J=7.7 Hz, 1H); 7.48 (broad m, 1H); 7.68 (broad m, 1H); 7.82 (d, J=7.7 Hz, 2H); 8.10 (broad d, J=2.9 Hz, 1H); 12.14 (s, 1H); 13.2 (broad m, 1H) for the predominant E or Z isomer.

Mass spectrum (LC/MS Method A): Retention time Tr (min)=3.65; [M+H]$^+$: m/z 319; [M−H]$^-$: m/z 317.

Stage 6:

In a 100 ml round-bottomed flask, 90 mg of 5-(6-fluoro-1H-benzimidazol-2-yl)pyrrolo[1,2-a]indol-9-one oxime obtained according to the preceding stage, in a mixture of 2 ml of acetic acid, 2 ml of ethanol and 2 ml of water, are stirred at ambient temperature. 19 mg of powdered zinc are added and the stirring is maintained for ½ hour. The reaction medium is filtered through clarcel, and washed with 80 ml of methanol, and the filtrate is evaporated to dryness under vacuum. The residue is chromatographed on silica gel (15-40 μm), elution being carried out with a mixture of methanol and dichloromethane (5/95 v/v). 42 mg of 5-(6-fluoro-1H-benzimidazol-2-yl)-9H-pyrrolo[1,2-a]indol-9-ylamine acetate are obtained in the form of a beige solid, the characteristics of which are the following:

1H NMR spectrum (400 MHz, δ in ppm, DMSO-d6): 1.89 (s, 3H); 4.93 (s, 1H); 6.08 to 6.20 (m, 2H); 7.12 (broad t, J=9.5 Hz, 1H); 7.24 to 7.80 (very broad m, 2H); 7.29 (t, J=7.8 Hz, 1H); 7.53 (broad s, 1H); 7.64 (broad d, J=7.8 Hz, 1H); 7.71 (broad d, J=7.8 Hz, 1H); 13.08 (broad m, 1H).

Mass spectrum (LC/MS Method A): Retention time Tr (min)=2.51; [M+H]$^+$: m/z 305; [M+H—NH3]$^+$: m/z 288 (base peak); [M−H]$^-$: m/z 303.

Stage 7:

A mixture of 42 mg of 5-(6-fluoro-1H-benzimidazol-2-yl)-9H-pyrrolo[1,2-a]indol-9-ylamine acetate obtained according to the preceding stage, 19 mg of 1H-pyrrolo[2,3-b]pyridine-4-carboxylic acid (which can be obtained according to WO 2003/000688), 39 mg of o-((ethoxycarbonyl)cyanomethylene-amino)-N,N,N',N'-tetramethyluronium tetrafluoroborate (TOTU) and 16 μl of diisopropylethylamine in 3 ml of N-methylpyrrolidone is stirred in a 100 ml round-bottomed flask. After 1 hour, the reaction medium is evaporated to dryness, the residue is taken up with 30 ml of a saturated solution of sodium bicarbonate and the aqueous phase is extracted with 4 times 30 ml of ethyl acetate. The combined organic phases are washed with 3 times 30 ml of a saturated solution of sodium chloride, dried over magnesium sulphate, and evaporated to dryness under vacuum. The residue is chromatographed on silica gel (15-40 μm), elution being carried out with a gradient of methanol (2% to 5% v/v) in dichloromethane, and then on a second column of silica gel (15-40 μm), elution being carried out with pure ethyl acetate. 12 mg of 1H-pyrrolo[2,3-b]pyridine-4-carboxylic acid [5-(6-fluoro-1H-benzimidazol-2-yl)-9H-pyrrolo[1,2-a]indol-9-yl]amide are obtained in the form of a brown solid, the characteristics of which are the following:

1H NMR spectrum: (400 MHz, δ in ppm, DMSO-d6): 6.22 to 6.28 (m, 2H); 6.40 (d, J=7.8 Hz, 1H); 6.89 (dd, J=3.4 and 2.0 Hz, 1H); 7.13 (broad m, 1H); 7.33 (t, J=7.6 Hz, 1H); 7.38 (broad m, 1H); 7.44 (d, J=4.9 Hz, 1H); 7.52 to 7.83 (m, 5H); 8.28 (d, J=4.9 Hz, 1H); 9.30 (d, J=7.8 Hz, 1H); 11.85 (broad m, 1H); 13.14 (s, 1H).

Mass spectrum (LC/MS Method A): Retention time Tr (min)=3.53; [M+H]$^+$: m/z 449; [2M+H]$^+$: m/z 897; [M+2H+CH$_3$CN]$_2^+$: m/z 245.5 (base peak).

Example 2

Synthesis of 1H-pyrrolo[2,3-b]pyridine-4-carboxylic acid (5-quinolin-3-yl-9H-pyrrolo[1,2-a]indol-9-yl) amide

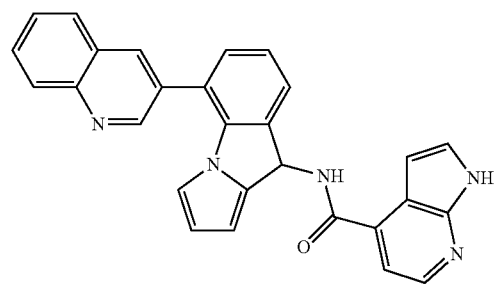

Stage 1:

In a 100 ml round-bottomed flask under argon, a mixture of 361 mg of 5-iodopyrrolo[1,2-a]indol-9-one (which can be prepared according to J. Med. Chem. 2004, 47(6), 1448), 214 mg of 3-quinolineboronic acid, 603 mg of caesium carbonate and 143 mg of tetrakis(triphenylphosphine)palladium(O) in 20 ml of dimethylformamide is heated at 123° C. After 3 hours, the reaction medium is evaporated to dryness under vacuum and the residue is taken up in ethyl acetate and filtered. The filtrate is washed with water, twice with a saturated solution of sodium bicarbonate and then with a saturated solution of sodium chloride, dried with magnesium sulphate, and evaporated to dryness under vacuum. The residue is chromatographed on silica gel (15-40 μm), elution being carried out with a gradient of ethyl acetate (20% to 30% v/v) in n-heptane. 231 mg of 5-quinolin-3-ylpyrrolo[1,2-a]indol-9-one are obtained in the form of a solid, the characteristics of which are the following:

1H NMR spectrum: (400 MHz, δ in ppm, CDCl$_3$): 6.08 (dd, J=3.8 and 2.6 Hz, 1H); 6.33 (dd, J=2.6 and 0.9 Hz, 1H); 6.80 (dd, J=3.8 and 0.9 Hz, 1H); 7.27 (t, J=7.7 Hz, 1H); 7.41 (dd, J=7.7 and 1.3 Hz, 1H); 7.65 to 7.72 (m, 2H); 7.85 (m, 1H); 7.92 (broad d, J=8.3 Hz, 1H); 8.24 (broad d, J=8.3 Hz, 1H); 8.32 (d, J=2.2 Hz, 1H); 9.07 (d, J=2.2 Hz, 1H).

Stage 2:

In a 100 ml round-bottomed flask, a mixture of 231 mg of 5-quinolin-3-ylpyrrolo[1,2-a]indol-9-one obtained according to the preceding stage and 164 mg of hydroxylamine hydrochloride in 20 ml of pyridine is refluxed under argon. After heating for 1.5 hours, the reaction medium is evaporated to dryness under vacuum. The residue is taken up in a saturated solution of sodium bicarbonate and extracted twice with ethyl acetate. The combined organic phases are washed with a saturated solution of sodium bicarbonate and then a saturated solution of sodium chloride, dried over magnesium sulphate, and evaporated to dryness under vacuum. The residue is chromatographed on silica gel (15-40 μm), elution being carried out with a gradient of methanol (2% to 3% v/v) in dichloromethane. 277 mg of 5-quinolin-3-ylpyrrolo[1,2-a]indol-9-one oxime hydrochloride are obtained in the form of a yellowish solid, the characteristics of which are the following:

1H NMR spectrum: (400 MHz, δ in ppm, DMSO-d6): 6.20 (dd, J=3.5 and 2.9 Hz, 1H); 6.24 (dd, J=2.9 and 1.1 Hz, 1H); 6.72 (dd, J=3.5 and 1.1 Hz, 1H); 7.34 (t, J=7.7 Hz, 1H); 7.47 (dd, J=7.7 and 1.3 Hz, 1H); 7.72 (m, 1H); 7.78 (dd, J=7.7 and 1.3 Hz, 1H); 7.88 (m, 1H); 8.10 (broad d, 25 J=7.9 Hz, 1H); 8.15 (broad d, J=7.9 Hz, 1H); 8.62 (d, J=2.2 Hz, 1H); 9.06 (d, J=2.2 Hz, 1H); 12.18 (broad m, 1H) for the predominant E or Z isomer.

Stage 3:

In a 100 ml round-bottomed flask, a mixture of 277 mg of 5-quinolin-3-ylpyrrolo[1,2-a]indol-9-one oxime hydrochloride obtained according to the preceding stage, in 5 ml of acetic acid, 5 ml of ethanol and 5 ml of water, is stirred at ambient temperature. 58 mg of powdered zinc are added and the resulting mixture is left to stir for 1.5 hours. A further 58 mg of powdered zinc is added and the resulting mixture is left to stir for 3.5 hours. The reaction medium is filtered through clarcel, washing being carried out with 100 ml of methanol. The filtrate is evaporated to dryness under vacuum and chromatographed on silica gel (15-40 μm), elution being carried out with a gradient of methanol (2% to 7% v/v) in dichloromethane. 116 mg of 5-quinolin-3-yl-9H-pyrrolo[1,2-a]indol-9-ylamine acetate are obtained in the form of a brown solid, the characteristics of which are the following:

1H NMR spectrum: (300 MHz, δ in ppm, DMSO-d6): 1.89 (s, 3H); 4.96 (s, 1H); 5.98 (broad d, J=3.1 Hz, 1H); 6.05 (t, J=3.1 Hz, 1H); 6.14 (dt, J=3.1 and 1.2 Hz, 1H); 7.28 (t, J=7.5 Hz, 1H); 7.35 (dd, J=7.5 and 1.2 Hz, 1H); 7.65 to 7.74 (m, 2H); 7.86 (m, 1H); 8.09 (broad d, J=8.0 Hz, 1H); 8.14 (broad d, J=8.0 Hz, 1H); 8.53 (d, J=2.3 Hz, 1H); 9.00 (d, J=2.3 Hz, 1H).

Stage 4:

In a 100 ml round-bottomed flask under argon, a mixture of 116 mg of 5-quinolin-3-yl-9H-pyrrolo[1,2-a]indol-9-ylamine acetate obtained according to the preceding stage, 63 mg of 1H-pyrrolo[2,3-b]pyridine-4-carboxylic acid (which can be obtained according to WO 2003/000688), 82 mg of N-(3-dimethylaminopropyl)-N'-ethylcarbodiimide hydrochloride (EDCI) and 58 mg of 1-hydroxybenzotriazole (HOBt) in 7.5 ml of dimethylformamide is stirred at ambient temperature for 18 hours. The reaction medium is evaporated to dryness under vacuum, 50 ml of water are added to the residue, and the suspension is stirred for 1 hour. The solid is filtered and washed with water, then with a saturated solution of sodium bicarbonate and again with water. The resulting product is spin-filter-dried overnight and then the solid is taken up in a mixture of methanol and dichloromethane (10/90 v/v), and the solvent is evaporated to dryness under vacuum. The residue is chromatographed on silica gel (15-40 μm), elution being carried out with a mixture of methanol and dichloromethane (3/97 v/v). 53 mg of 1H-pyrrolo[2,3-b]pyridine-4-carboxylic acid (5-quinolin-3-yl-9H-pyrrolo[1,2-a]indol-9-yl)amide are obtained in the form of a beige solid, the characteristics of which are the following:

1H NMR spectrum: (300 MHz, δ in ppm, DMSO-d6): 6.09 (broad d, J=3.2 Hz, 1H); 6.13 (t, J=3.2 Hz, 1H); 6.24 (dm, J=3.2 Hz, 1H); 6.44 (broad d, J=8.3 Hz, 1H); 6.90 (broad d, J=3.3 Hz, 1H); 7.32 (t, J=7.7 Hz, 1H); 7.41 to 7.47 (m, 2H); 7.60 to 7.67 (m, 2H); 7.73 (m, 1H); 7.88 (m, 1H); 8.10 to 8.18 (m, 2H); 8.29 (d, J=5.0 Hz, 1H); 8.57 (broad m, 1H); 9.04 (broad m, 1H); 9.33 (d, J=8.3 Hz, 1H); 11.89 (broad m, 1H).

Mass spectrum (LC/MS Method C): Retention time Tr (min)=2.36; [M+H]⁺: m/z 442; [M−H]⁻: m/z 440.

Example 3

Synthesis of 1H-pyrrolo[2,3-b]pyridine-4-carboxylic acid [5-(3H-imidazo[4,5-c]pyridin-2-yl)-9H-pyrrolo[1,2-a]indol-9-yl]amide

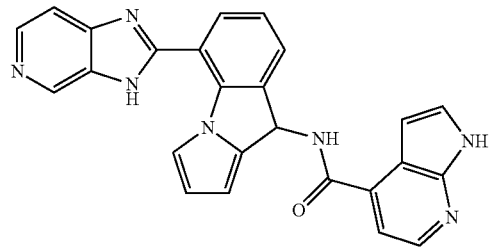

Stage 1:

In a 500 ml round-bottomed flask, a mixture of 730 mg of 9-oxo-9H-pyrrolo[1,2-a]indole-5-carboxylic acid obtained according to stage 2 of Example 1, 373 mg of 3,4-diaminopyridine, 721 mg of N-(3-dimethylaminopropyl)-N'-ethylcarbodiimide hydrochloride (EDCI) and 508 mg of 1-hydroxybenzotriazole (HOBt) in 60 ml of dimethylformamide is stirred for 19 hours at ambient temperature. The reaction medium is evaporated to dryness under vacuum and the solid residue is taken up in 50 ml of water. The precipitate is filtered off and the solid is washed successively with 3 times 80 ml of water, 3 times 80 ml of a saturated solution of sodium bicarbonate and again with 3 times 80 ml of water. The solid is dissolved in methanol and the solvent is evaporated to dryness under vacuum. The residue is chromatographed on silica gel (15-40 μm), elution being carried out with a gradient of methanol (5% to 10% v/v) in dichloromethane and then a mixture of dichloromethane and 5N ammoniacal methanol (90/10 v/v). 220 mg of 9-oxo-9H-pyrrolo[1,2-a]indole-5-carboxylic acid (4-aminopyridin-3-yl)amide are obtained in the form of a solid, the characteristics of which are the following:

1H NMR spectrum: (400 MHz, δ in ppm, DMSO-d6): 6.02 (broad s, 2H); 6.35 (dd, J=3.7 and 2.7 Hz, 1H); 6.66 (d, J=5.6 Hz, 1H); 6.92 (dd, J=3.7 and 1.1 Hz, 1H); 7.33 (t, J=7.7 Hz, 1H); 7.58 (dd, J=2.7 and 1.1 Hz, 1H); 7.68 (dd, J=7.7 and 1.3 Hz, 1H); 7.95 (d, J=5.6 Hz, 1H); 8.00 (dd, J=7.7 and 1.3 Hz, 1H); 8.15 (s, 1H); 10.00 (broad s, 1H).

Stage 2:

In a 20 ml microwave reactor, a mixture of 256 mg of 9-oxo-9H-pyrrolo[1,2-a]indole-5-carboxylic acid (4-aminopyridin-3-yl)amide obtained according to the preceding stage, in 20 ml of glacial acetic acid, is heated at 200° C. for 30 minutes. The reaction medium is filtered through clarcel, washing being carried out with glacial acetic acid. The filtrate is evaporated to dryness under vacuum and the residue is taken up twice with toluene and each time re-evaporated to dryness under vacuum. The solid is triturated from isopropyl ether, filtered, and dried under vacuum at 40° C. overnight. 111 mg of 5-(3H-imidazo[4,5-c]pyridin-2-yl)pyrrolo[1,2-a]indol-9-one are obtained in the form of a solid, the characteristics of which are the following:

1H NMR spectrum: (400 MHz, δ in ppm, DMSO-d6): 6.38 (dd, J=3.9 and 2.6 Hz, 1H); 6.98 (dd, J=3.9 and 1.1 Hz, 1H); 7.43 (t, J=7.6 Hz, 1H); 7.72 (dd, J=7.6 and 1.4 Hz, 1H); 7.76

(broad d, J=5.6 Hz, 1H); 8.11 (broad d, J=7.6 Hz, 1H); 8.38 (d, J=5.6 Hz, 1H); 8.50 (broad m, 1H); 9.11 (broad s, 1H); 13.8 (very broad m, 1H).

Stage 3:

In a 250 ml round-bottomed flask under argon, a mixture of 444 mg of 5-(3H-imidazo[4,5-c]pyridin-2-yl)pyrrolo[1,2-a]indol-9-one obtained according to the preceding stage and 323 mg of hydroxylamine hydrochloride in 60 ml of pyridine is refluxed for 3 hours. The reaction medium is evaporated to dryness under vacuum, the residue is taken up in a saturated solution of sodium bicarbonate and the precipitate is filtered off and washed with water. The solid is dissolved in methanol and the solvent is evaporated to dryness under vacuum. The residue is taken up in toluene and then re-evaporated to dryness under vacuum. 380 mg of 5-(3H-imidazo[4,5-c]pyridin-2-yl)pyrrolo[1,2-a]indol-9-one oxime are obtained in the form of a solid, the characteristics of which are the following:

1H NMR spectrum: (400 MHz, δ in ppm, DMSO-d6): 6.25 (dd, J=3.5 and 2.9 Hz, 1H); 6.72 (dd, J=3.5 and 1.3 Hz, 1H); 7.18 (t, J=7.7 Hz, 1H); 7.34 (dd, J=5.5 and 1.2 Hz, 1H); 7.59 (dd, J=7.7 and 1.4 Hz, 1H); 7.86 (d, J=5.5 Hz, 1H); 8.29 (dd, J=7.7 and 1.4 Hz, 1H); 8.69 (d, J=1.2 Hz, 1H); 9.23 (dd, J=2.9 and 1.3 Hz, 1H) for the predominant E or Z isomer.

Stage 4:

In a 100 ml round-bottomed flask, a mixture of 200 mg of 5-(3H-imidazo[4,5-c]pyridin-2-yl)pyrrolo[1,2-a]indol-9-one oxime obtained according to the preceding stage, in 5 ml of glacial acetic acid, 5 ml of ethanol and 5 ml of water, is stirred at ambient temperature. 43 mg of powdered zinc are added and the stirring is maintained at ambient temperature for 2 hours. The reaction medium is filtered through clarcel, washing being carried out with methanol. The filtrate is evaporated to dryness under vacuum and the residue is chromatographed on silica gel (15-40 μm), elution being carried out with a mixture of dichloromethane and 5N ammoniacal methanol (95/5 v/v). 51 mg of 5-(3H-imidazo[4,5-c]pyridin-2-yl)-9H-pyrrolo[1,2-a]indol-9-ylamine are obtained in the form of a solid, the characteristics of which are the following:

1H NMR spectrum: (400 MHz, δ in ppm, DMSO-d6): 4.94 (s, 1H); 6.14 to 6.20 (m, 2H); 7.31 (t, J=7.6 Hz, 1H); 7.54 (broad s, 1H); 7.64 (d, J=5.6 Hz, 1H); 7.70 (d, J=7.6 Hz, 1H); 7.74 (d, J=7.6 Hz, 1H); 8.36 (d, J=5.6 Hz, 1H); 9.01 (s, 1H).

Mass spectrum (LC/MS Method A): Retention time Tr (min)=0.32; [M+H]⁺: m/z 288; [M+H–NH₃]⁺: m/z 271; [M–H]⁻: m/z 286.

Stage 5:

In a 100 ml round-bottomed flask, a mixture of 51 mg of 5-(3H-imidazo[4,5-c]pyridin-2-yl)-9H-pyrrolo[1,2-a]indol-9-ylamine obtained according to the preceding stage, 28 mg of 1H-pyrrolo[2,3-b]pyridine-4-carboxylic acid (which can be obtained according to WO 2003/000688), 37 mg of N-(3-dimethylaminopropyl)-N'-ethylcarbodiimide hydrochloride (EDCI) and 26 mg of 1-hydroxybenzotriazole (HOBt) in 5 ml of dimethylformamide is stirred for 4 hours under argon at ambient temperature. The reaction medium is evaporated to dryness under vacuum. The residue is triturated from 20 ml of water and then filtered. The solid is washed with a saturated solution of sodium bicarbonate and taken up in a mixture of dichloromethane and methanol, and the solution is evaporated to dryness under vacuum. The residue is chromatographed on silica gel (15-40 μm), elution being carried out with a mixture of dichloromethane and methanol (98/2 v/v). 47 mg of 1H-pyrrolo[2,3-b]pyridine-4-carboxylic acid [5-(3H-imidazo[4,5-c]pyridin-2-yl)-9H-pyrrolo[1,2-a]indol-9-yl]amide are obtained in the form of a solid, the characteristics of which are the following:

1H NMR spectrum: (400 MHz, δ in ppm, DMSO-d6): 6.22 to 6.28 (m, 2H); 6.40 (d, J=8.2 Hz, 1H); 6.89 (dd, J=3.4 and 2.0 Hz, 1H); 7.33 (t, J=7.7 Hz, 1H); 7.44 (d, J=5.1 Hz, 1H); 7.61 (dd, J=3.4 and 2.5 Hz, 1H); 7.64 (d, J=6.2 Hz, 1H); 7.67 (broad d, J=7.7 Hz, 1H); 7.84 (d, J=7.7 Hz, 1H); 7.85 (broad m, 1H); 8.28 (d, J=5.1 Hz, 1H); 8.33 (d, J=6.2 Hz, 1H); 9.01 (s, 1H); 9.29 (d, J=8.2 Hz, 1H); 11.84 (broad m, 1H); 13.47 (broad m, 1H).

Mass spectrum (LC/MS Method A): Retention time Tr (min)=2.39; [M+H]⁺: m/z 432; [M–H]⁻: m/z 430.

Example 4

Synthesis of 6-chloro-1H-pyrrolo[2,3-b]pyridine-4-carboxylic acid [5-(3H-imidazo[4,5-c]pyridin-2-yl)-9H-pyrrolo[1,2-a]indol-9-yl]amide

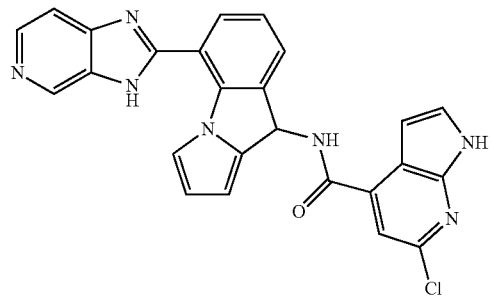

Stage 1:

In a 100 ml three-necked flask, a solution of 1.55 g of 3-chloroperoxy-benzoic acid in 5 ml of ethyl acetate is added, in the space of 5 minutes under argon at −5° C., to a mixture of 881 mg of methyl ester of 1H-pyrrolo[2,3-b]pyridine-4-carboxylic acid (which can be obtained according to WO 2003/000688) in 10 ml of ethyl acetate. After stirring for 1 hour at −5° C., the mixture is allowed to return to ambient temperature. The brown solid is filtered off, washed with 3 times 3 ml of ethyl acetate and dried. 844 mg of 7-oxy-1H-pyrrolo[2,3-b]pyridine-4-carboxylic acid methyl ester are obtained in the form of a brown solid, the characteristics of which are the following:

1H NMR spectrum: (400 MHz, δ in ppm, DMSO-d6): 3.93 (s, 3H); 6.93 (d, J=2.9 Hz, 1H); 7.63 (d, J=2.9 Hz, 1H); 7.64 (d, J=6.8 Hz, 1H); 8.23 (d, J=6.8 Hz, 1H); 12.79 (broad m, 1H).

Mass spectrum (LC/MS Method A): Retention time Tr (min)=1.97; [M+H]⁺: m/z 193; [M–H]⁻: m/z 191.

Stage 2:

In a 100 ml three-necked flask, 2.17 ml of methanesulphonyl chloride are added, dropwise, while maintaining the temperature below 25° C., to a suspension of 4.49 g of 7-oxy-1H-pyrrolo[2,3-b]pyridine-4-carboxylic acid methyl ester obtained according to the preceding stage, in 30 ml of dimethylformamide. The reaction medium is then heated at 80° C. for 1 hour. After cooling, a further 2.17 ml of methanesulphonyl chloride are added while maintaining the temperature below 35° C. The reaction medium is again heated at 80° C. for 1 hour. After cooling, 50 ml of water are added while maintaining the temperature below 30° C. The very viscous reaction medium is cooled to 5° C. and the precipitate is filtered off. The beige solid is washed with 5 times 15 ml of water and dried. 3.53 g of 6-chloro-1H-pyrrolo[2,3-b]pyridine-4-carboxylic acid methyl ester are obtained in the form of a beige solid, the characteristics of which are the following:

1H NMR spectrum: (400 MHz, δ in ppm, DMSO-d6): 3.96 (s, 3H); 6.88 (dd, J=3.4 and 2.0 Hz, 1H); 7.57 (s, 1H); 7.75 (dd, J=3.4 and 2.5 Hz, 1H); 12.27 (broad m, 1H).

Stage 3:

In a 100 ml round-bottomed flask, 7.5 ml of a 1M aqueous solution of lithium hydroxide are added, at ambient temperature, to a suspension of 527 mg of 6-chloro-1H-pyrrolo[2,3-b]pyridine-4-carboxylic acid methyl ester obtained according to the preceding stage, in 15 ml of methanol. After stirring for 2.5 hours at ambient temperature, 7.5 ml of 1N hydrochloric acid are added dropwise. After stirring for ½ hour, the solid is filtered off, washed with 25 ml of water and dried. 475 mg of 6-chloro-1H-pyrrolo[2,3-b]pyridine-4-carboxylic acid are obtained in the form of a beige solid, the characteristics of which are the following:

1H NMR spectrum: (400 MHz, δ in ppm, DMSO-d6): 6.87 (dd, J=3.4 and 2.0 Hz, 1H); 7.53 (s, 1H); 7.70 (dd, J=3.4 and 2.5 Hz, 1H); 12.19 (broad m, 1H); 13.66 (very broad m, 1H).

Mass spectrum (LC/MS Method A): Retention time Tr (min)=2.35; [M+H]$^+$: m/z 197; [M−H]$^−$: m/z 195.

Stage 4:

In a 100 ml round-bottomed flask, a mixture of 69 mg of 5-(3H-imidazo[4,5-c]pyridin-2-yl)-9H-pyrrolo[1,2-a]indol-9-ylamine obtained according to stage 4 of Example 3, 48 mg of 6-chloro-1H-pyrrolo[2,3-b]pyridine-4-carboxylic acid obtained according to the preceding stage, 51 mg of N-(3-dimethylaminopropyl)-N'-ethylcarbodiimide hydrochloride (EDCI) and 36 mg of 1-hydroxybenzotriazole (HOBt) in 5 ml of dimethylformamide is stirred for 3 hours under argon at ambient temperature. The reaction medium is evaporated to dryness under vacuum and the residue is chromatographed on silica gel (15-40 µm), elution being carried out with a gradient of methanol (4% to 6% v/v) in dichloromethane. The valuable fractions are combined and evaporated to dryness under vacuum, the residue is triturated from a solution of sodium bicarbonate and filtered, and the solid is washed with water. The precipitate is dissolved in methanol and the solvent is evaporated to dryness under vacuum. 11 mg of 6-chloro-1H-pyrrolo[2,3-b]pyridine-4-carboxylic acid [5-(3H-imidazo[4,5-c]pyridin-2-yl)-9H-pyrrolo[1,2-a]indol-9-yl]amide are obtained in the form of a solid, the characteristics of which are the following:

1H NMR spectrum: (300 MHz, δ in ppm, DMSO-d6): 6.21 to 6.28 (m, 2H); 6.36 (broad d, J=8.3 Hz, 1H); 6.91 (d, J=3.7 Hz, 1H); 7.31 (t, J=7.8 Hz, 1H); 7.54 (s, 1H); 7.56 to 7.68 (m, 3H); 7.90 (broad d, J=7.8 Hz, 1H); 8.04 (broad m, 1H); 8.26 (d, J=6.0 Hz, 1H); 8.96 (s, 1H); 9.43 (d, J=8.3 Hz, 1H); 12.08 (broad m, 1H).

Mass spectrum (LC/MS Method D): Retention time Tr (min)=0.59; [M+H]$^+$: m/z 466; [M−H]$^−$: m/z 464.

Example 5

Pharmaceutical Composition

Tablets corresponding to the following formula were prepared:

| | |
|---|---|
| Product of Example 1 | 0.2 g |
| Excipient for a tablet with a final weight of | 1 g |
| (details of the excipient: lactose, talc, starch, magnesium stearate). | |

The present invention also comprises all the pharmaceutical compositions prepared with any product of formula (I) according to the present invention.

Biological Tests for Biologically Characterizing the Products of the Invention:

The inorganic phosphate released during the hydrolysis of ATP by the ATPase activity of Hsp82 is quantified by the malachite green method. In the presence of this reagent, formation of the inorganic phosphate-molybdate-malachite green complex, which absorbs at a wavelength of 620 nm, occurs.

The products to be evaluated are incubated in a reaction volume of 30 µl, in the presence of 1 µM Hsp82 and of 250 µM of substrate (ATP) in a buffer composed of 50 mM Hepes-NaOH (pH 7.5), 1 mM DTT, 5 mM MgCl$_2$ and 50 mM KCl at 37° C. for 60 min. In parallel, an inorganic phosphate range of between 1 and 40 µM is made up in the same buffer. The ATPase activity is then revealed by adding 60 µl of the biomol green reagent (Tebu). After incubation at ambient temperature for 20 min, the absorbents of the various wells is measured using a microplate reader at 620 nm. The inorganic phosphate concentration of each sample is then calculated from the standard curve.

The ATPase activity of Hsp82 is expressed as concentration of inorganic phosphate produced in 60 minutes. The effect of the various products tested is expressed as percentage inhibition of the ATPase activity.

The formation of ADP due to the ATPase activity of Hsp82 was used to develop another method for evaluating the enzymatic activity of this enzyme by application of an enzymatic coupling system involving pyruvate kinase (PK) and lactate dehydrogenase (LDH). In this kinetic-type spectrophotometric method, PK catalyses the formation of ATP and of pyruvate from phosphoenol pyruvate (PEP) and the ADP produced by Hsp82. The pyruvate formed, which is a substrate for LDH, is subsequently converted to lactate in the presence of NADH. In this case, the decrease in NADH concentration, measured through the decrease in absorbance at the wavelength of 340 nm, is proportional to the concentration of ADP produced by Hsp82.

The products tested are incubated in a reaction volume of 100 µl of buffer composed of 100 mM Hepes-NaOH (pH 7.5), 5 mM MgCl$_2$, 1 mM DTT, 150 mM KCl, 0.3 mM NADH, 2.5 mM PEP and 250 µM ATP. This mixture is preincubated at 37° C. for 30 minutes before the addition of 3.77 units of LDH and 3.77 units of PK. The reaction is initiated by addition of the product to be evaluated, in varying concentrations, and of Hsp82, at the concentration of 1 µM. The enzymatic activity of Hsp82 is then measured continuously, in a microplate reader, at 37° C., at the wavelength of 340 nm. The initial rate of the reaction is obtained by measuring the slope of the tangent to the origin of the curve recorded. The enzymatic activity is expressed in µM of ADP formed per minute. The effect of the various products tested is expressed as capacity for inhibiting the ATPase activity according to the codification below:

A: IC50<1 µM

B: 1 µM<IC50<10 µM

C: 10 µM<IC50<100 µM

TABLE OF RESULTS

| Ex | Structure | Hsp82 ATPase IC50 μM |
|---|---|---|
| 1 | 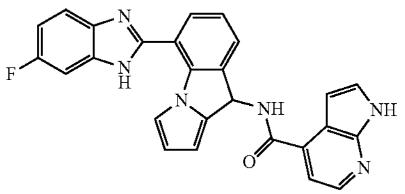 | A |
| 2 | 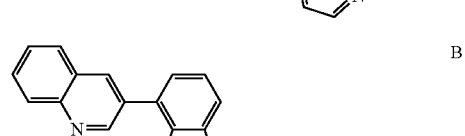 | B |
| 3 | 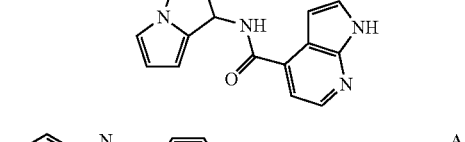 | A |
| 4 | 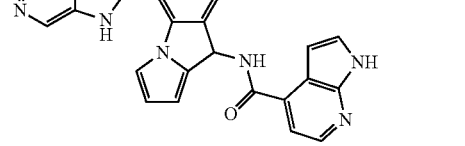 | B |

The invention claimed is:

1. A compound according to formula (I)

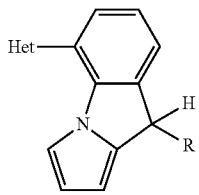

in which:

Het represents a monocyclic or bicyclic, aromatic or partially unsaturated heterocycle—of dihydro or tetrahydro type—, with from 5 to 11 ring members, containing from 1 to 4 heteroatoms chosen from N, O or S, optionally substituted with one or more radicals R1 or R'1, which may be identical or different;

R is chosen from the group consisting of X-(A-B)$_n$—CONH$_2$, X-(A-B)$_n$—O—CONH$_2$, X-(A-B)$_n$—NH—CONH$_2$, X—(CH$_2$)$_m$-heterocycloalkyl, X—(CH$_2$)$_m$-aryl and X—(CH$_2$)$_m$-heteroaryl where X represents —O—C(O), —NH—C(O), NH—CS, —NH—CO—CH$_2$—O—; —NH—CO—CH$_2$—S—CH$_2$—CO—NH—; —NH—CO—(CH$_2$)$_2$—SO$_2$—; —NH—CO—CH$_2$—N(CH$_3$)—CO—; A and B, which may be identical or different, independently represent a single bond, CH$_2$, CH-alkyl or CH-aralkyl, n=1 or 2 and m=0 or 1; and R1 and R'1, which may be identical or different, are selected from the group consisting of H, halogen, CF$_3$, nitro, cyano, alkyl, hydroxyl, mercapto, amino, alkylamino, dialkylamino, alkoxy, alkylthio, carboxyl in free form or esterified with an alkyl radical, carboxamide, CO—NH(alkyl), CON(alkyl)$_2$, NH—CO-alkyl, sulphonamide, NH—SO$_2$-alkyl, S(O)$_2$—NHalkyl and S(O)$_2$—N(alkyl)$_2$, all the alkyl, alkoxy and alkylthio radicals being themselves optionally substituted with one or more radicals, which may be identical or different, chosen from halogen, hydroxyl, alkoxy, amino, alkylamino and dialkylamino;

or a pharmaceutically acceptable salt thereof.

2. A compound according to claim 1, in which:

Het is chosen from the group consisting of:

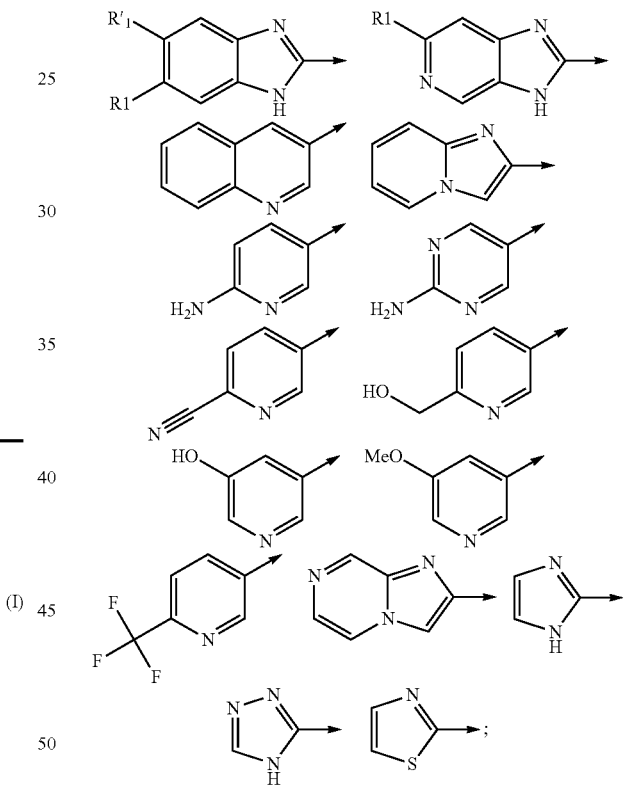

and

R1 and R'1, which may be identical or different, are selected from the group consisting of H, halogen, CF$_3$, nitro, cyano, alkyl, hydroxyl, mercapto, amino, alkylamino, dialkylamino, alkoxy, alkylthio (methylthio), carboxyl in free form or esterified with an alkyl radical, carboxamide, CO—NH(alkyl) and CON(alkyl)$_2$, NH—CO-alkyl, sulphonamide, NH—SO$_2$-alkyl, S(O)$_2$—NHalkyl and S(O)$_2$—N(alkyl)$_2$, all the alkyl, alkoxy and alkylthio radicals being themselves optionally substituted with one or more radicals, which may be identical or different, chosen from halogen, hydroxyl, alkoxy, amino, alkylamino and dialkylamino;

or a pharmaceutically acceptable salt thereof.

3. A compound according to claim 2, in which R is chosen from the group consisting of:
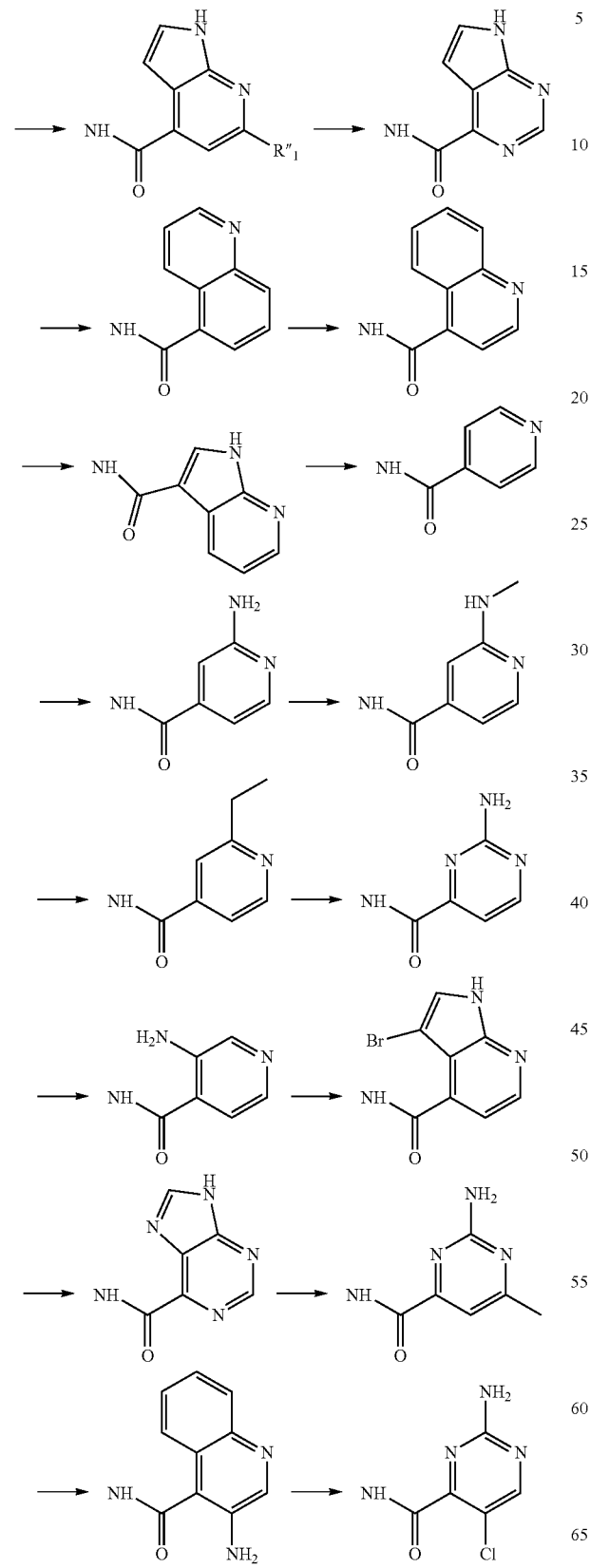
or a pharmaceutically acceptable salt thereof.
4. A compound according to claim 1, in which:
Het is chosen from the group consisting of:
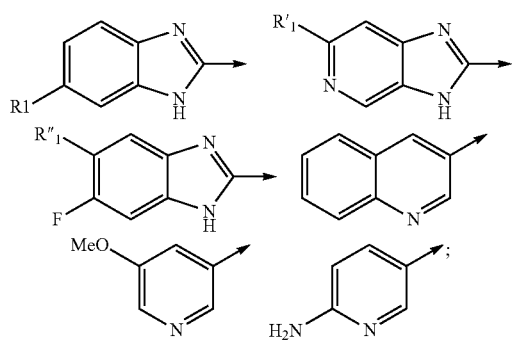
R is chosen from the group consisting of:
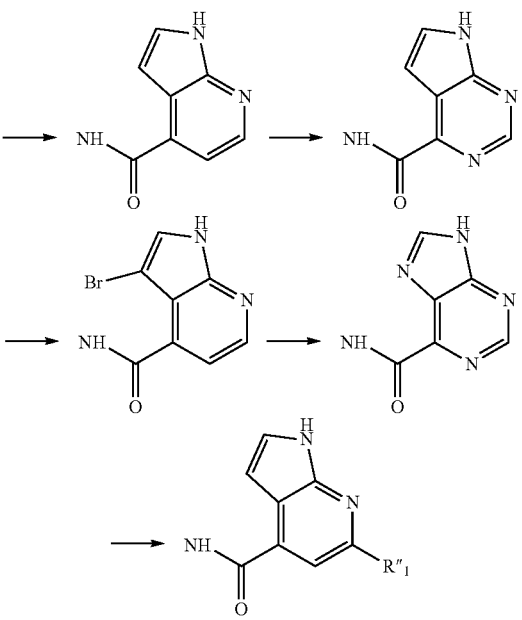

R1 is in the group consisting of H, F, Cl, Br, CF₃, NO₂, CN, CH₃, OH, OCH₃, OCF₃, CO₂Me, CONH₂, CONHMe, CONH—(CH₂)₃—OMe, CONH—(CH₂)₃—N(Me)₂, NHC(O)Me, SO₂NH₂ and SO₂N(Me)₂;

R'1 is in the group consisting of H, CONH₂, CONHMe and OMe; and

R"1 is in the group consisting of F, Cl, OH, OMe, CN, O—(CH₂)₃—OMe and O—(CH₂)₃—N(Me)₂;

or a pharmaceutically acceptable salt thereof.

5. A compound according to claim 1, in which:

Het is chosen from the group consisting of:

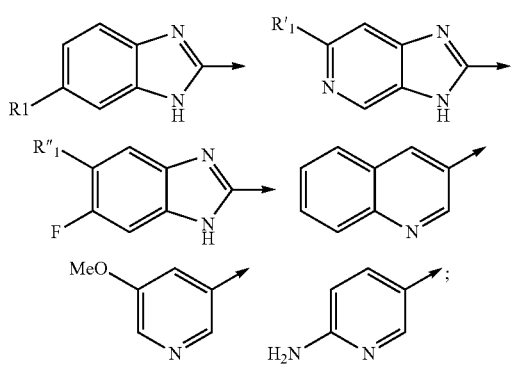

R is chosen from the group consisting of:

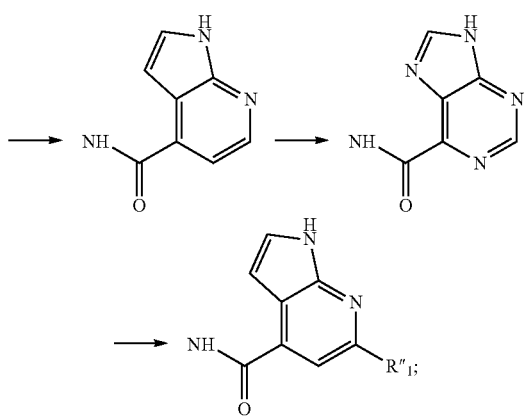

R1 is in the group consisting of H, F, Cl, Br, CF₃, NO₂, CN, CH₃, OH, OCH₃, OCF₃, CO₂Me, CONH₂, CONHMe, CONH—(CH₂)₃—OMe, CONH—(CH₂)₃—N(Me)₂, NHC(O)Me, SO₂NH₂ and SO₂N(Me)₂, R'1 is in the group consisting of H, CONH₂, CONHMe and OMe, and R"1 is in the group consisting of F, Cl, OH, OMe, CN, O—(CH₂)₃—OMe and O—(CH₂)₃—N(Me)₂;

or a pharmaceutically acceptable salt thereof.

6. A compound according to claim 1, in which:

Het is chosen from the group consisting of:

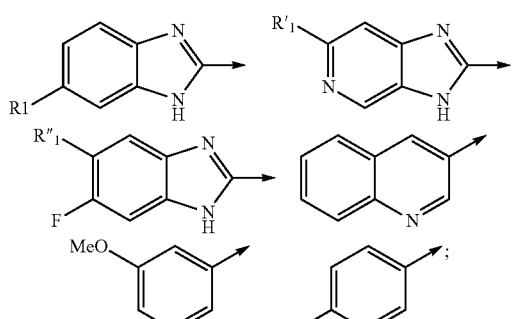

R1 represents H, F, Cl, Br, CF₃, NO₂, CN, CH₃, OH, OCH₃, OCF₃, CO₂Me, CONH₂, CONHMe, CONH—(CH₂)₃—OMe, CONH—(CH₂)₃—N(Me)₂, NHC(O)Me, SO₂NH₂ or SO₂N(Me)₂;

R'1 represents H, CONH₂, CONHMe or OMe;

R"1 represents F, Cl, OH, OMe, CN, O—(CH₂)₃—OMe or O—(CH₂)₃—N(Me)₂; and

R is chosen from the group consisting of:

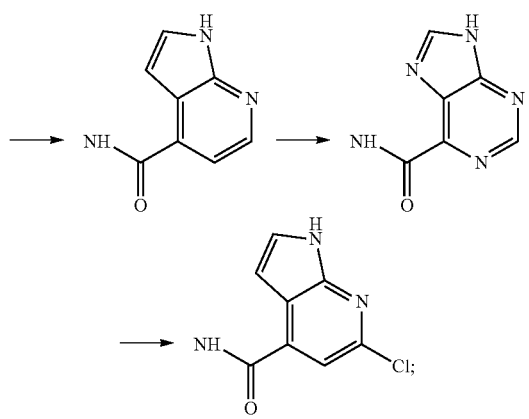

or a pharmaceutically acceptable salt thereof.

7. A compound selected from the group consisting of:

1H-pyrrolo[2,3-b]pyridine-4-carboxylic acid [5-(6-fluoro-1H-benzimidazol-2-yl)-9H-pyrrolo[1,2-a]indol-9-yl]amide;

1H-pyrrolo[2,3-b]pyridine-4-carboxylic acid (5-quinolin-3-yl-9H-pyrrolo[1,2-a]indol-9-yl)amide;

1H-pyrrolo[2,3-b]pyridine-4-carboxylic acid [5-(3H-imidazo[4,5-c]pyridin-2-yl)-9H-pyrrolo[1,2-a]indol-9-yl]amide; and 6-chloro-1H-pyrrolo[2,3-b]pyridine-4-carboxylicacid [5-(3H-imidazo[4,5-c]pyridin-2-yl)-9H-pyrrolo[1,2-a]indol-9-yl]amide;

or a pharmaceutically acceptable salt thereof.

8. A pharmaceutical composition comprising a compound according to claim 1 or a pharmaceutically acceptable salt thereof.

* * * * *